(12) United States Patent
Eikenberg

(10) Patent No.: US 7,010,089 B2
(45) Date of Patent: Mar. 7, 2006

(54) DIGITAL RADIOGRAPHIC SENSOR VIEW CAPTURE

(75) Inventor: Steven L. Eikenberg, Ft. Knox, KY (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/409,722

(22) Filed: Apr. 8, 2003

(65) Prior Publication Data

US 2004/0037391 A1    Feb. 26, 2004

Related U.S. Application Data

(63) Continuation of application No. 09/954,678, filed on Sep. 14, 2001, now Pat. No. 6,628,751.

(60) Provisional application No. 60/235,159, filed on Sep. 22, 2000.

(51) Int. Cl.
*H05G 1/64* (2006.01)

(52) U.S. Cl. .................................. 378/98.12; 378/191
(58) Field of Classification Search ............ 378/38–40, 378/98.8, 98.12, 189–191
See application file for complete search history.

(56) References Cited

U.S. PATENT DOCUMENTS

| | | | |
|---|---|---|---|
| 4,554,676 A | 11/1985 | Maldonado et al. | 378/170 |
| 5,416,822 A * | 5/1995 | Kunik | 378/162 |
| 5,485,500 A | 1/1996 | Baba et al. | 378/98.2 |
| 5,995,583 A * | 11/1999 | Schick et al. | 378/38 |
| 6,000,743 A | 12/1999 | Hart | 296/70 |
| 6,002,743 A | 12/1999 | Telymonde | 378/98.8 |
| 6,215,848 B1 | 4/2001 | Linders et al. | 378/98.12 |

FOREIGN PATENT DOCUMENTS

WO    WO 00/36820    6/2000

* cited by examiner

*Primary Examiner*—Craig E. Church
*Assistant Examiner*—Jurie Yun
(74) *Attorney, Agent, or Firm*—Elizabeth Arwine

(57) ABSTRACT

An apparatus including but not limited to a charge-coupled device(CCD)-array sensor positioning mechanism, the positioning mechanism structured to position a CCD-array sensor to capture a first target area; and the CCD-array sensor positioning mechanism further structured to position the CCD-array sensor to capture a second target area proximate to the first target area, the first and second target areas spatially related such that a first radiographic image recorded at the first target area may be combined with a second radiographic image recorded at the second target area to form a composite radiographic image substantially analogous to a single radiographic image of an aggregate target area covered by the first and second target areas.

28 Claims, 27 Drawing Sheets

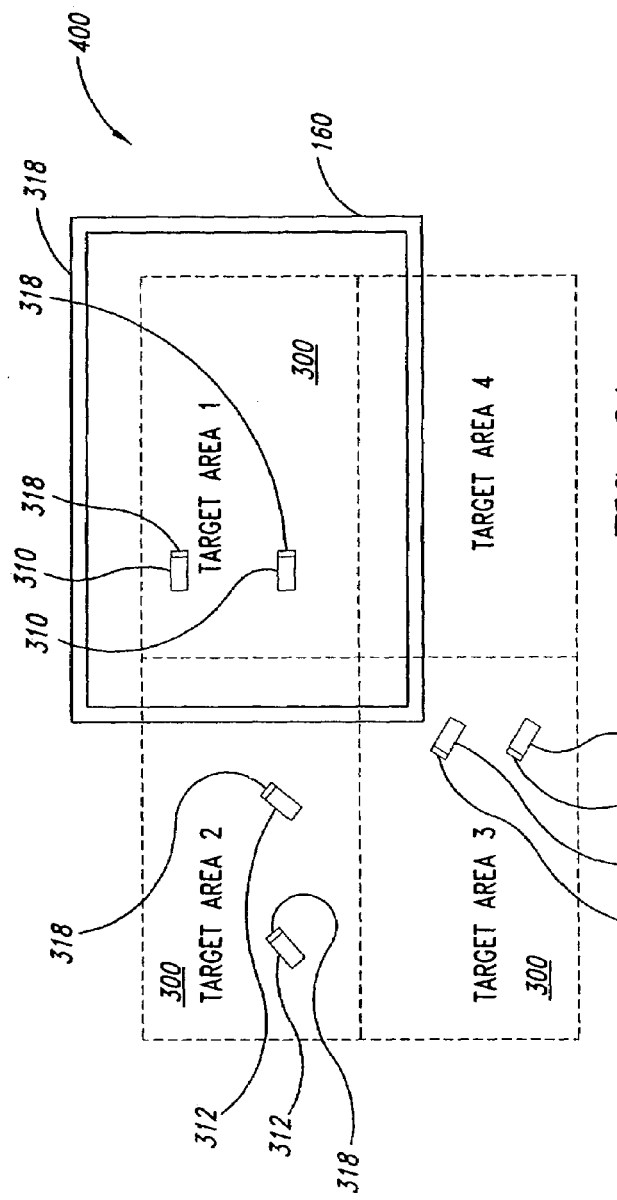
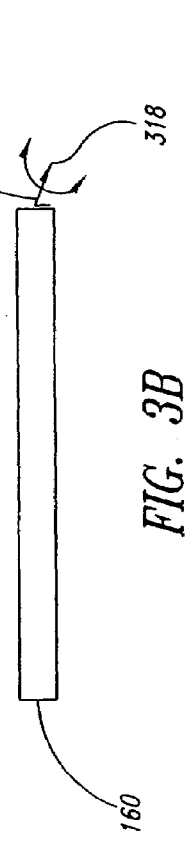
FIG. 3A
FIG. 3B

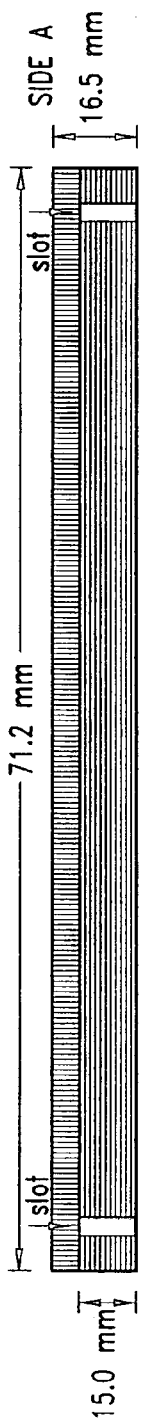
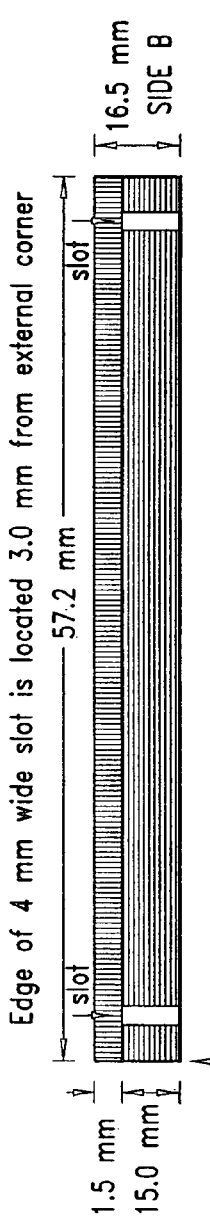
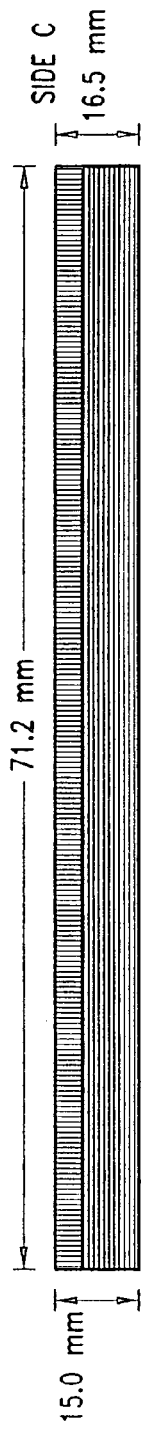
FIG. 5B
FIG. 5C
FIG. 5D
FIG. 5E

Plastic Positioning Block for SOPD, option one
Positioning block for New Image/Dentsply and Dexis Companies
All supports are 5mm high x 4mm x 4mm

Dentsply/New Image and Dexis #2 Digital Sensor

Top surface, area to be exposed to x-ray beam

Bottom surface, where cord connects to sensor. This surface is placed opposite the x-ray source.

Sensor size compared to image size

Side view of sensor

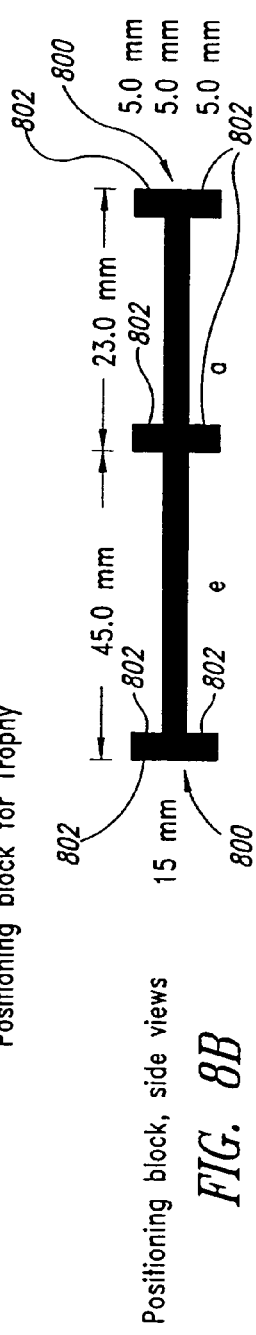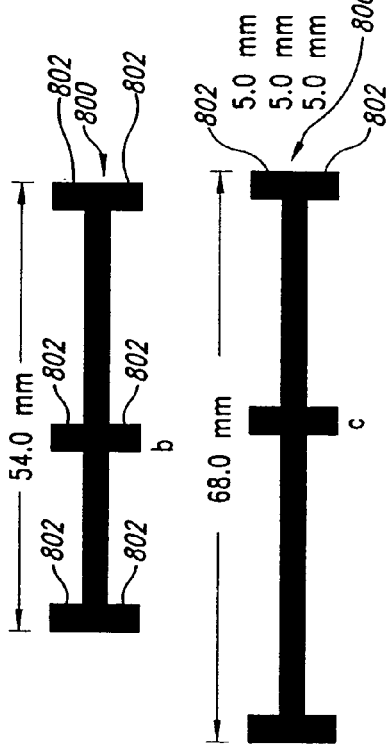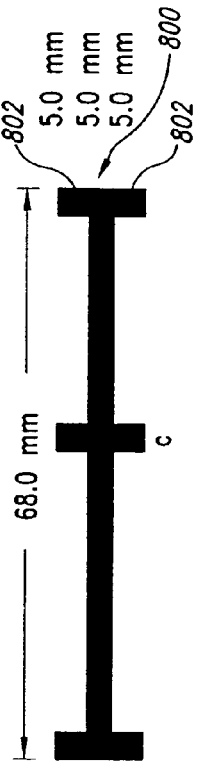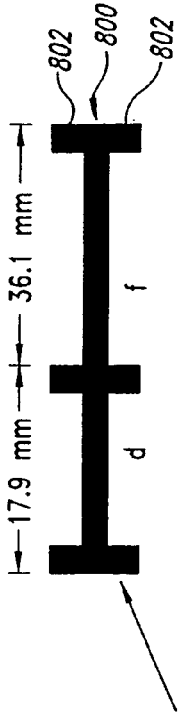
Plastic Positioning Blocks for SOPD, option one
FIG. 8B Positioning block, side views / Positioning block for Trophy
FIG. 8C
FIG. 8D
FIG. 8E All supports are 5mm high x 4mm x 4mm Trophy #2 Digital Sensor 36.1 mm
45.0 mm Top surface, area to be exposed to x-ray beam Bottom surface, where cord connects to sensor. This surface is placed opposite the x-ray source.

4.8 mm
1.95 mm
26.5 mm
35.9 mm
1.95 mm
Target Area or Image Capture Area
4.8 mm

Sensor size compared to image size 12.0 mm
7.0 mm

Side view of sensor

Plastic Positioning Block for SOPD, option one

Positioning block for Schick

All supports are 5mm high x 4mm x 4mm

Schick #2 Digital Sensor

Top surface, area to be exposed to x-ray beam

Bottom surface, where cord connects to sensor. This surface is placed opposite the x-ray source.

Side view of sensor

Sensor size compared to image size

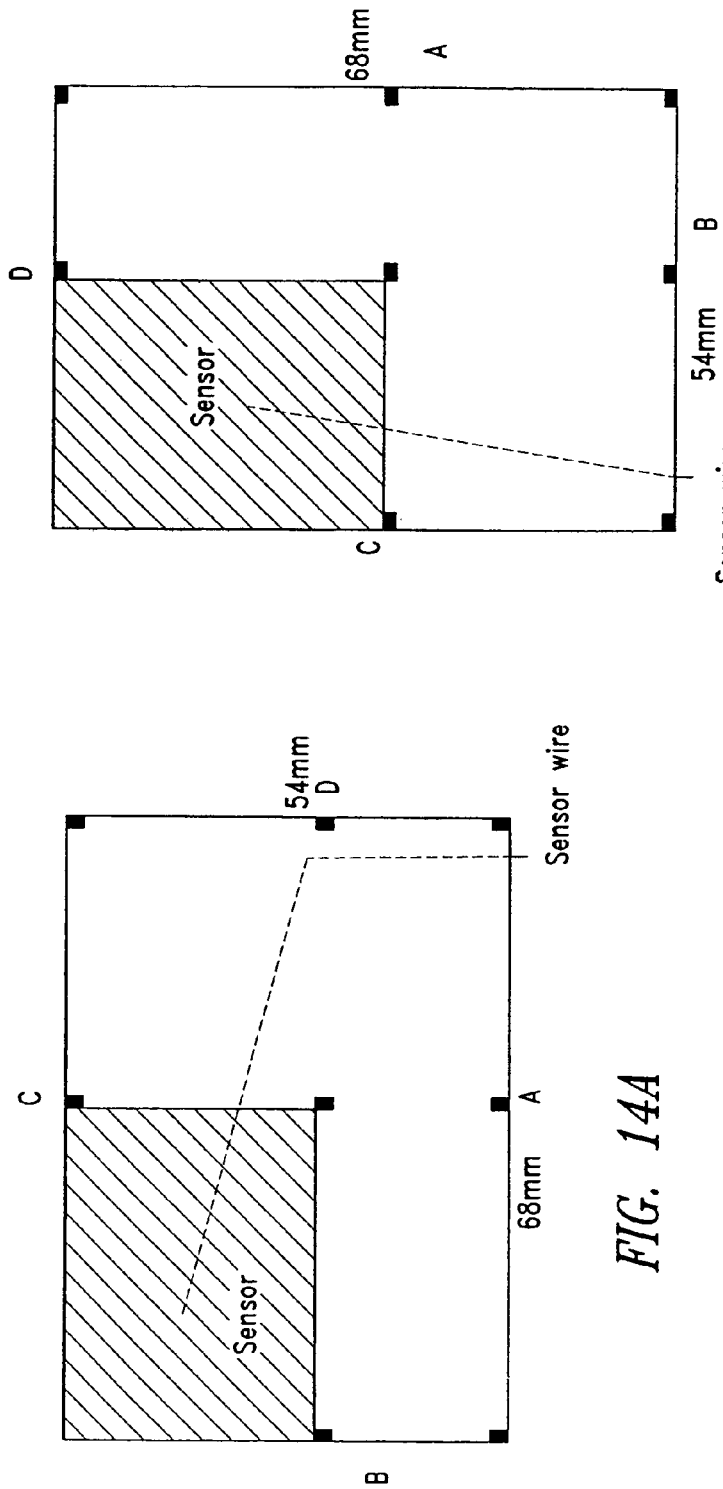

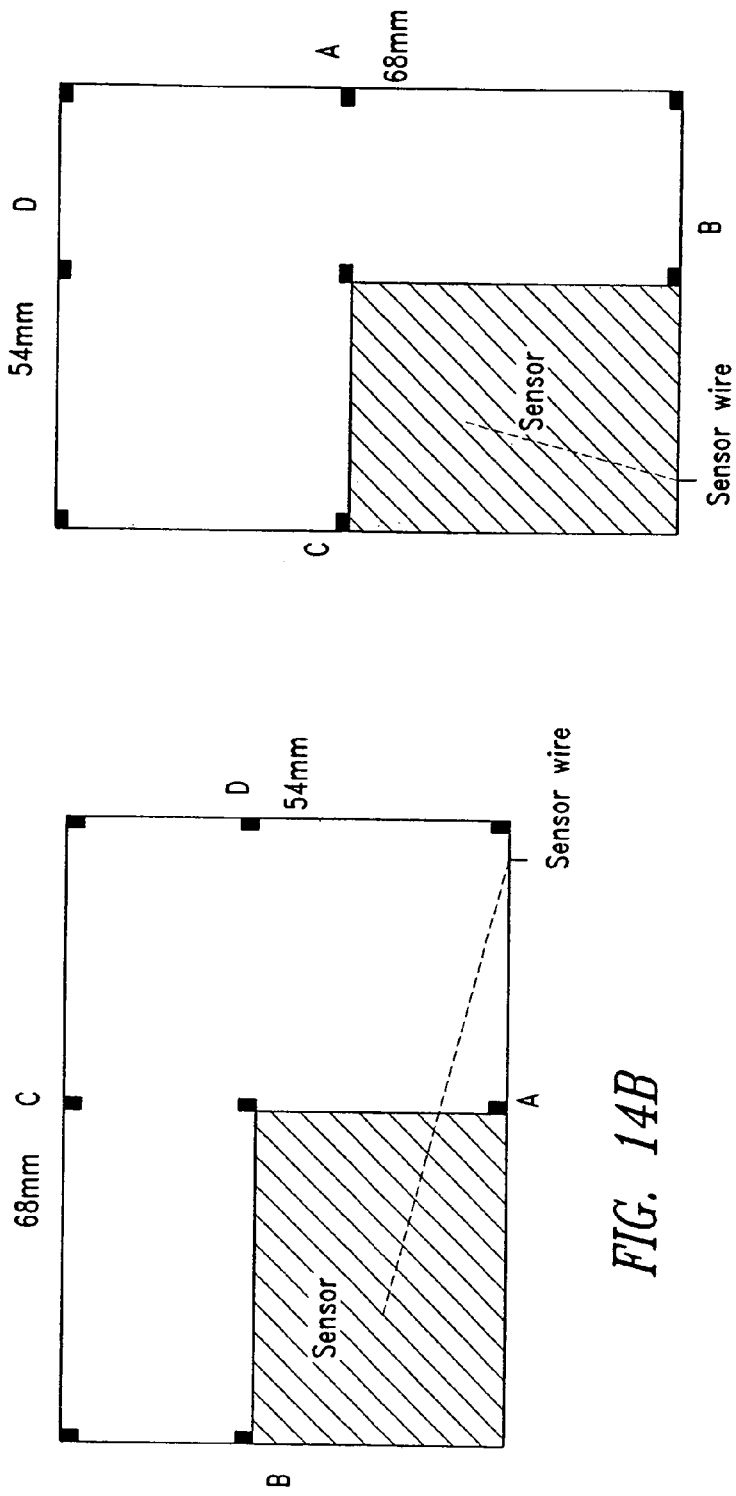

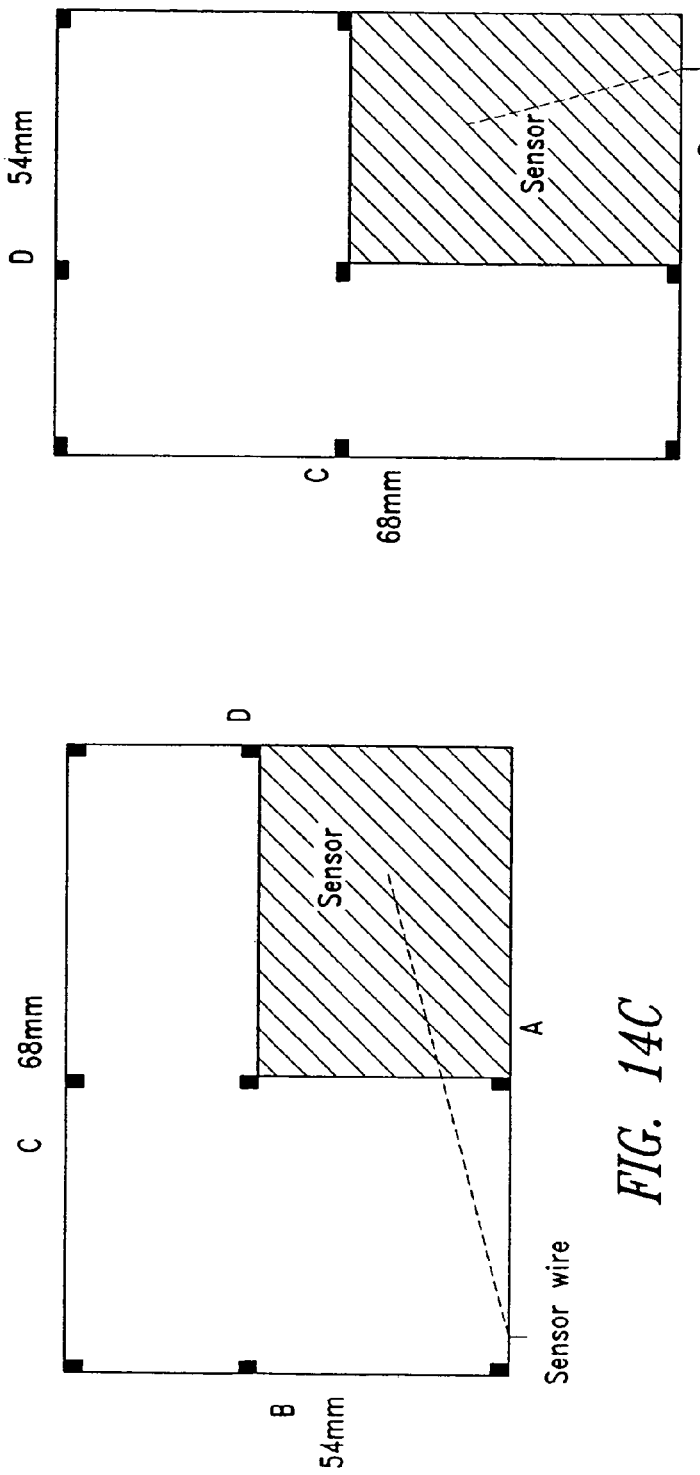

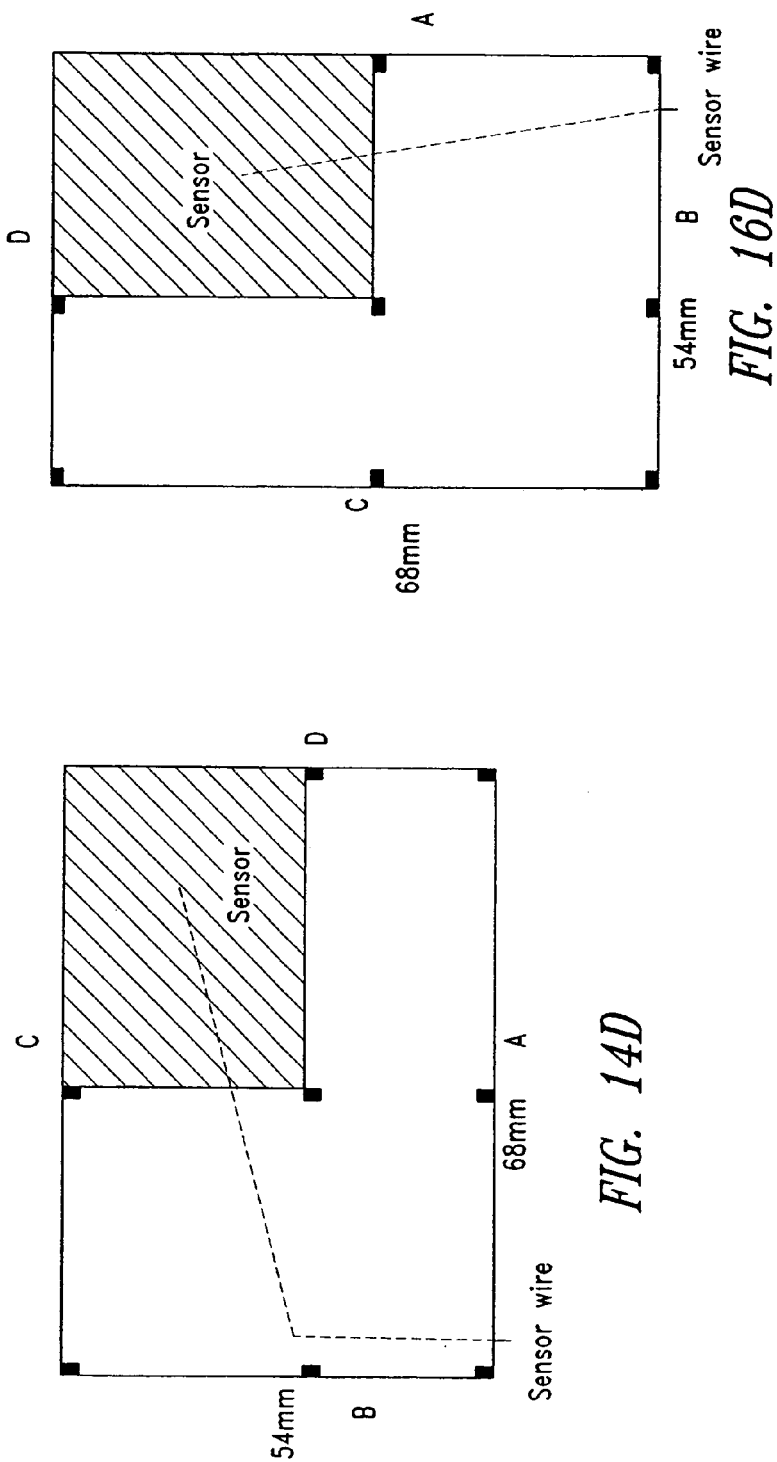

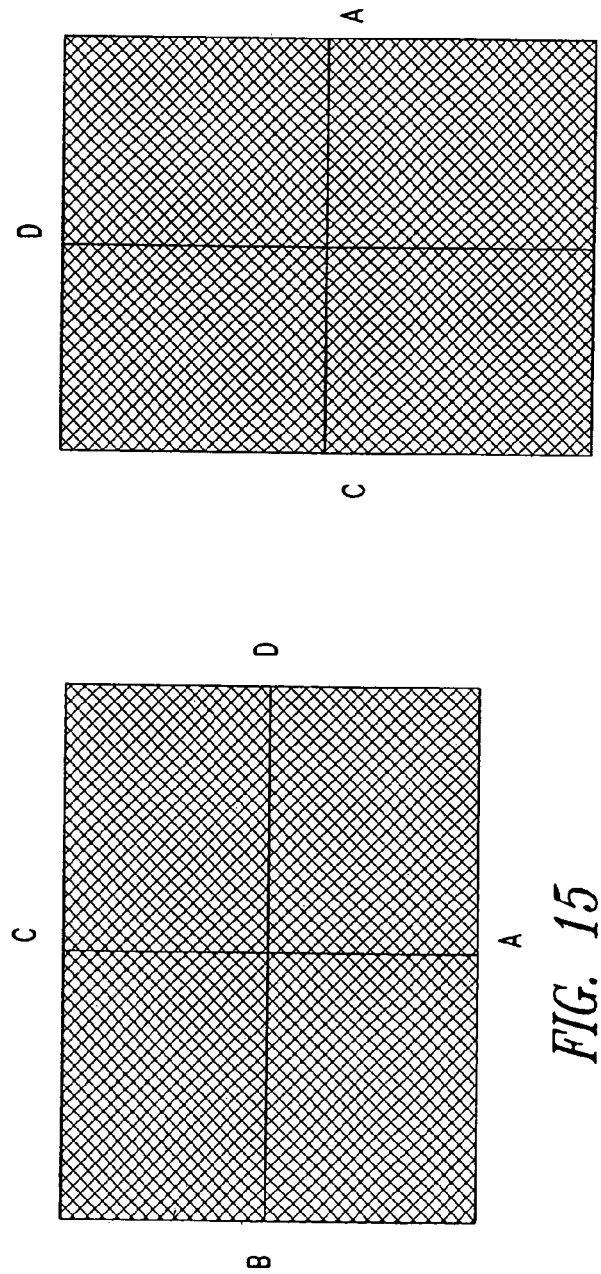

1

DIGITAL RADIOGRAPHIC SENSOR VIEW CAPTURE

CROSS-REFERENCE(S) TO RELATED APPLICATION(S)

This application is a continuation of U.S. patent application Ser. No. 09/954,678 filed Sep. 14, 2001 now U.S. Pat. No. 6,628,751, which claims the benefit under 35 U.S.C. § 119(e) of U.S. Provisional Application No. 60/235,159 filed Sep. 22, 2002, which are hereby incorporated by reference.

STATEMENT REGARDING FEDERALLY SPONSORED RESEARCH OR DEVELOPMENT

This invention was made with government support provided by the United States Army. The government has certain rights in this invention.

BACKGROUND OF THE INVENTION

1. Field of the Invention

The devices and processes described herein relate, in general, to dental imaging systems.

2. Description of the Related Art

Dental imaging systems are systems that obtain, manipulate, process, and electronically store and display dental image data. A Computerized Digital Radiography (CDR) system constitutes an example of dental imaging systems.

Non-CDR dental imaging systems traditionally use radiographic film to obtain and capture dental images. Non-CDR dental imaging systems can capture a number of traditional "views" of a patient's teeth and associated bony structures. Three such traditional views upon which dental professionals heavily rely are the bitewing, periapical, and occlusal views.

Unlike non-CDR systems, CDR systems utilize charge-coupled device (CCD) array sensors, rather than radiographic film, to directly obtain digital dental images. Since CDR systems allow the dental images to be captured directly to digital form, such CDR systems effect the "paperless" dental office, in that the images are stored in digital format (e.g., on CD-ROM or magnetic disk drive) rather than film. Readily available commercial embodiments of such CDR systems may be obtained from several companies, such as Shick Technologies, of Long Island, N.Y.; Trophy Radiology Inc., of Marietta, Ga.; Dexis Dental, of Palo Alto, Calif.; and Dentsply International Inc.'s Gendex Division, of Des Plaines, Ill.

CDR systems have many advantages. Examples of such advantages are that CDR systems do not require radiographic film, nor do they require the processing capabilities and darkroom capabilities necessary to develop the radiographic film into a traditional radiograph, nor do they require traditional backlit radiographic viewers. However, CDR systems are not without disadvantages.

Significant disadvantages associated with CDR systems are associated with the extremely high financial and or technical costs associated with the engineering and production of the CDR-system CCD-array sensors. Those having ordinary skill in the art will recognize that while standard digital cameras use CCD-array sensors, and the cost of such CCD-array sensors is beginning to come down with mass production, the financial and or technical costs associated with engineering and producing CDR-system CCD-array sensors are now, and are expected to remain in the future, extremely high. One reason for such high financial and technical costs is that CDR system CCD-array sensors require much, much greater pixel resolution than standard digital camera CCDs. Non-CDR radiographic film has resolution of about 14 lines/millimeter (mm). Insofar as CDR system digital images are intended to replace the non-CDR radiographic film images, every effort is made in the industry to produce CDR-system CCD-array sensors capable of capturing a digital image having resolution comparable to the non-CDR system radiographic film. At present even though the industry has expended considerable financial and technical resources, the average resolution available with CDR-system CCD-array sensors is about 8 lines/mm; thus, currently available CDR-system CCD-array sensors tend to be very expensive due to expenditures associated with past efforts to achieve the resolution of the radiographic film and continuing efforts to continue to approach the resolution of the radiographic film.

Another reason for the high financial and technical costs associated with CDR-system CCD-array sensors is that CDR system CCD-array sensors require much, much greater gray-scale resolution than standard digital camera CCDs (each CCD-array sensor pixel has a value, proportional to the amount of absorbed radiation, which is converted to a grey level). Non-CDR radiographic film, being an extremely sensitive analog recording device, tends to reproduce gray scale shading with extremely high resolution. In contrast, CCD-array sensors, being digital recording devices, must produce the gray scale in steps (e.g., 0–264 "shades" of gray), and producing CCD-array sensors capable or such gray scale resolution also tends to be very financially and/or technically expensive, for reasons similar to those associated with the high pixel resolution requirement. Yet another reason for the high financial and technical costs associated with CDR-system CCD-array sensors is that CDR-system CCD-array sensors detect X-ray frequency photons, and since the energy per photon in X-rays is substantially greater than the energy per photon of visible light, the CDR-system CCD-array sensors must be able to withstand significantly more wear and tear than the CCD-array sensors used in the standard digital camera; thus, engineering and producing such rugged CCD-array sensors also tends to be relatively expensive financially and/or technically.

A consequence of the foregoing-described cost issues related to CCD arrays utilized in the CDR systems is that CDR systems do not, in general, provide readily available digital images of occlusal views because of the financial cost and technical difficulties associated with constructing CCD-array sensors of a size necessary to capture the views. The target area of occlusal views tends to be, on average, roughly four times (4×) the target area of CDR-system CCD-array sensors currently available. Because of the foregoing-noted technical issues associated with CDR-system CCD-array sensors, increasing the size of a CCD necessary to capture an image within a larger target is not a linear operation in either financial cost or technical difficulty. Rather, doubling the size of the target area to be captured by a CDR-system CCD-array sensor could have an associated cost/technical difficulty logarithmically proportional to that associated with the smaller target area, while quadrupling the target area could have an associated cost/technical difficulty logarithmically proportional to that associated with the smaller target area. Accordingly, due to financial and/or technical difficulty issues, CDR systems do not generally provide digital images of occlusal views, since the target area of such occlusal views tends to be, on average, roughly four times (4×) the target area of CDR system CCD-array sensors currently available.

Irrespective of the foregoing-noted difficulties, as noted above, dental professionals have a longstanding and ongoing reliance on occlusal view radiographic images. As also noted above, CDR systems have significant advantages over non-CDR systems. In light of the foregoing, the inventor named herein (inventor) has posited that if a method and apparatus could be devised which would allow the production of CDR-system digital images showing views over target areas which are in the same or different orientation as currently available images, but several multiples in size the currently available CDR system digital image views (e.g., occlusal views) in such a way that the foregoing-cataloged related-art financial and technical difficulties associated with constructing CDR-system CCD-array sensors capable of capturing such increased target areas are avoided, such a method and apparatus system would be extremely advantageous. Unfortunately, no such method and apparatus currently exist within the art.

SUMMARY OF THE INVENTION

The inventor has devised a method and mechanism which provide for the production of CDR-system digital images showing views several multiples in size of views which may be produced using currently available CDR system image technology (e.g., occlusal views), but where the production is done in such a way that the foregoing-cataloged related-art financial and technical difficulties associated with constructing CDR-system CCD-array sensors capable of capturing such increased target areas are avoided.

In one embodiment, the apparatus includes but is not limited to a charge-coupled device (CCD)-array sensor positioning mechanism, the positioning mechanism structured to position a CCD-array sensor to capture a first target area; and the CCD-array sensor positioning mechanism further structured to position the CCD-array sensor to capture a second target area proximate to the first target area, the first and second target areas spatially related such that a first radiographic image recorded at the first target area may be combined with a second radiographic image recorded at the second target area to form a composite radiographic image substantially analogous to a single radiographic image of an aggregate target area covered by the first and second target areas.

In one embodiment, a related method includes but is not limited to recording a first radiographic image of a first target area using CCD-array sensor techniques; recording a second radiographic image of a second target area, the second target area proximate to the first target area, using CCD-array sensor techniques; and displaying a composite image constructed from the first and second images.

The foregoing is a summary and thus contains, by necessity, simplifications, generalizations and omissions of detail; consequently, those skilled in the art will appreciate that the summary is illustrative only and is not intended to be in any way limiting. Other aspects, inventive features, and advantages of the devices and/or processes described herein, as defined solely by the claims, will become apparent in the non-limiting detailed description set forth herein.

BRIEF DESCRIPTION OF THE DRAWINGS

The devices and/or processes described herein may be better understood, and their numerous objects, features, and advantages made apparent to those skilled in the art by referencing the accompanying drawings.

FIG. 3A shows floor 300 of CCD-array sensor positioning device 400 (described in detail below) of CCD-array sensor positioning mechanism 100.

FIG. 3B shows a cut-away side plan view of CCD-array sensor positioning device 100, wherein shown is an exemplar of pop-up hinges 310, 312, and 314.

FIG. 5B depicts a cutaway side plan view of side A of stabilization portion 500.

FIG. 5C depicts a cutaway side plan view of side B of stabilization portion 500.

FIG. 5D depicts a cutaway side plan view of side C of stabilization portion 500.

FIG. 5E depicts a cutaway side plan view of side D of stabilization portion 500.

FIGS. 8B–8E depict side plane views of solid positioning block 800.

FIGS. 14–D respectively show four different examples of how a CCD-array sensor may be placed in CCD-array sensor device positioning mechanism 100 to capture a radiographic image of four different respectively proximate target areas.

FIG. 15 shows an example of how the respective images captured at the respectively proximate target areas of 14A-D can overlap.

FIGS. 16A–16D respectively show four different examples of how a CCD-array sensor may be placed in CCD-array sensor device positioning mechanism 100 to capture a radiographic image of four different respectively proximate target areas.

FIG. 17 shown is an example of how the respective images captured at the respectively proximate target areas of 16A–16D can overlap.

The use of the same reference symbols in different drawings indicates similar or identical items.

DESCRIPTION OF THE PREFERRED EMBODIMENT(S)

The following sets forth a detailed description for carrying out the devices and/or processes described herein. The description is intended to be illustrative and should not be taken to be limiting.

As noted in the summary, the inventor has devised a method and mechanism which provide for the production of CDR-system digital images showing views several multiples in size of views which may be produced using currently available CDR system image technology (e.g., occlusal views), but where the production is done in such a way that the foregoing-cataloged related-art financial and technical difficulties associated with constructing CDR-system CCD-array sensors capable of capturing such increased target areas are avoided. Implementations of the method and mechanism are described herein.

Figure 1A:
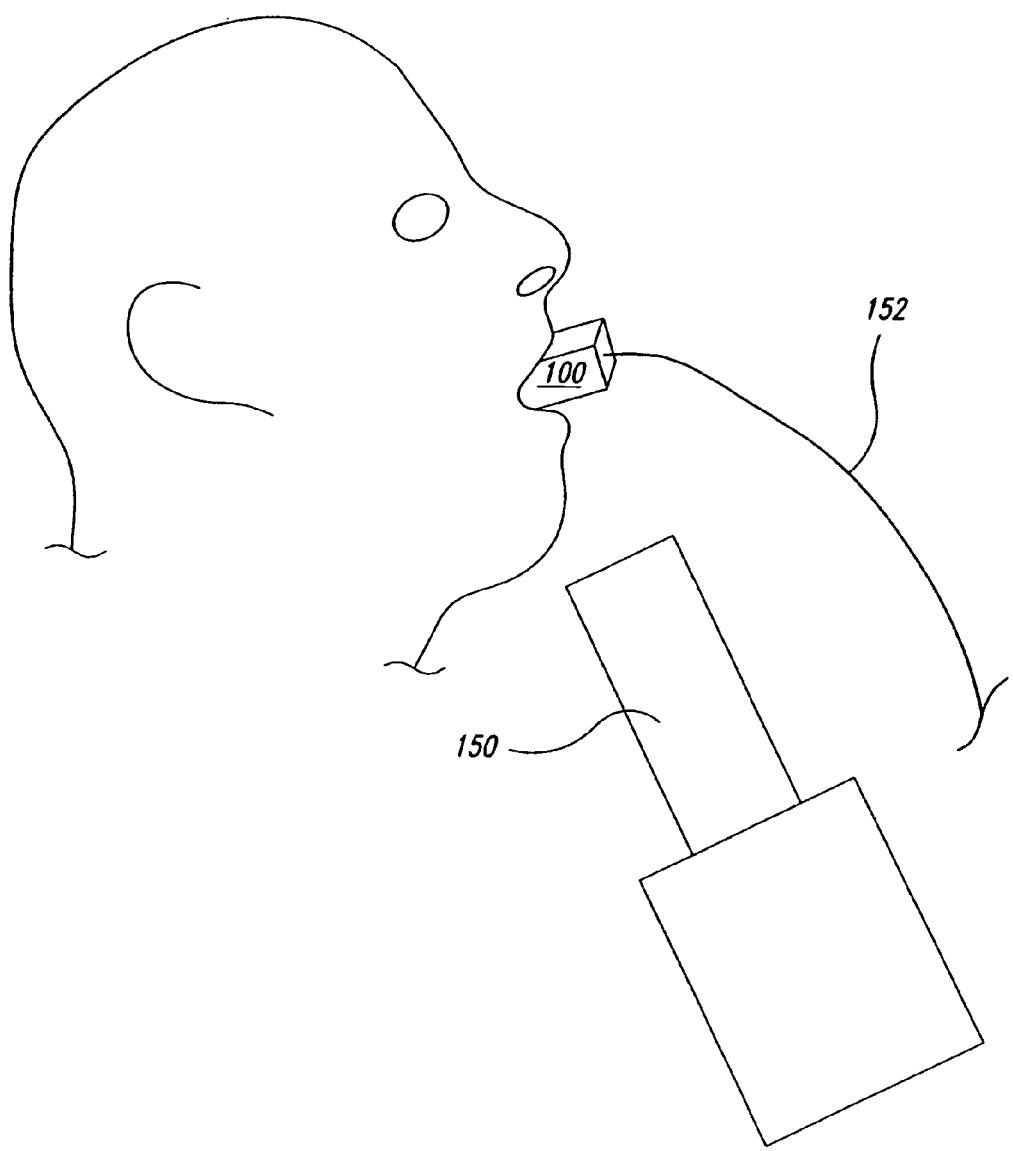
FIG. 1A shows a perspective view of an implementation of charge-coupled device (CCD)-array sensor positioning mechanism 100, depicted positioned on a dental patient to capture a mandibular occlusal radiographic view.

With reference to the figures, and with reference now to FIG. 1A, shown is a perspective view of an implementation of charge-coupled device (CCD)-array sensor positioning mechanism 100, depicted positioned on a dental patient to capture a mandibular occlusal radiographic view. Depicted is CCD-array sensor positioning mechanism 100 positioned such that cord 152 of a CCD-array sensor (which is internal to charge-coupled device CCD-array sensor positioning mechanism 100, and thus which cannot be seen in FIG. 1A, but which is situated in one of the various orientations, described below, to capture a radiographic image of a defined target area) exits away from the dental patient's mouth and such that the active surface (i.e., the surface that can record radiographic images) of the CCD-array sensor is oriented such that it will receive x-ray energy from x-ray tube 150 (i.e., the active side faces downward toward the patient's tongue). Illustrated is x-ray tube 150 proximate to the dental patient and aimed in a fashion substantially consistent with traditional aiming used to capture mandibular occlusal views on radiographic film. The radiographic image can then be captured using software and/or hardware available from many commercial companies, such as the imaging systems sold by Dexis Dental, of Palo Alto, Calif.

Figure 1B:
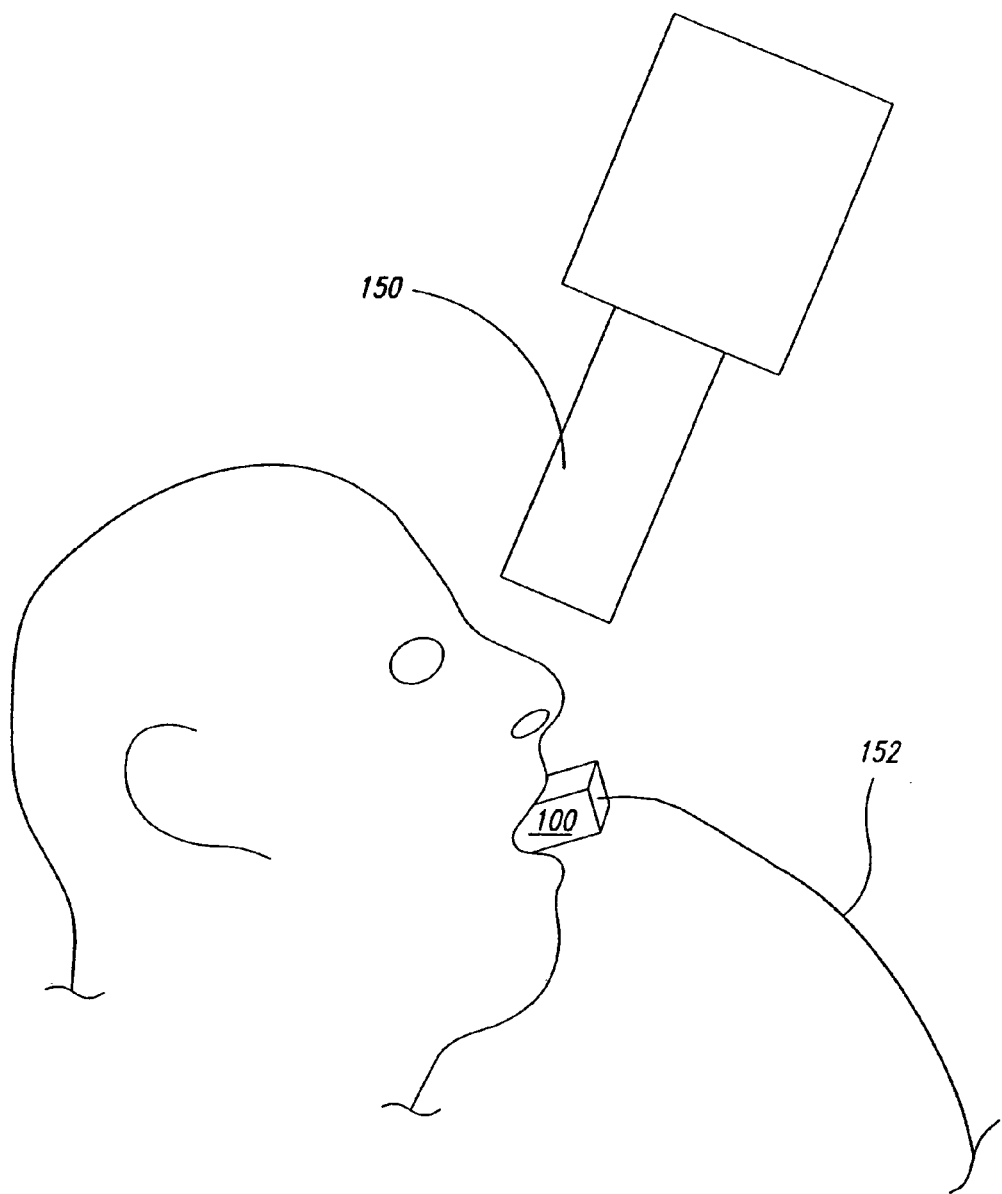
FIG. 1B shows a perspective view of an implementation of CCD-array sensor positioning mechanism 100, depicted positioned on a dental patient to capture a maxillary occlusal radiographic view.

Referring now to FIG. 1B, shown is a perspective view of an implementation of CCD-array sensor positioning mechanism 100, depicted positioned on a dental patient to capture a maxillary occlusal radiographic view. Depicted is CCD-array sensor positioning mechanism 100 positioned such that cord 152 of a CCD-array sensor (which is internal to charge-coupled device CCD-array sensor positioning mechanism 100, and thus which cannot be seen in FIG. 1B, but which situated in one of various orientations, described below, to capture a radiographic image of a defined target area) exits away from the dental patient's mouth and such that the active surface (i.e., the surface that can record radiographic images) is oriented such that it will receive the x-ray energy from x-ray tube 150 (i.e., the active side faces upward toward the roof of the patient's mouth). Illustrated is x-ray tube 150 proximate to the dental patient and aimed in a fashion substantially consistent with traditional aiming used to capture maxillary occlusal views on radiographic film. The radiographic image can then be captured using software and/or hardware available from many commercial companies, such as Dexis Dental, of Palo Alto, Calif.

Figure 1C:
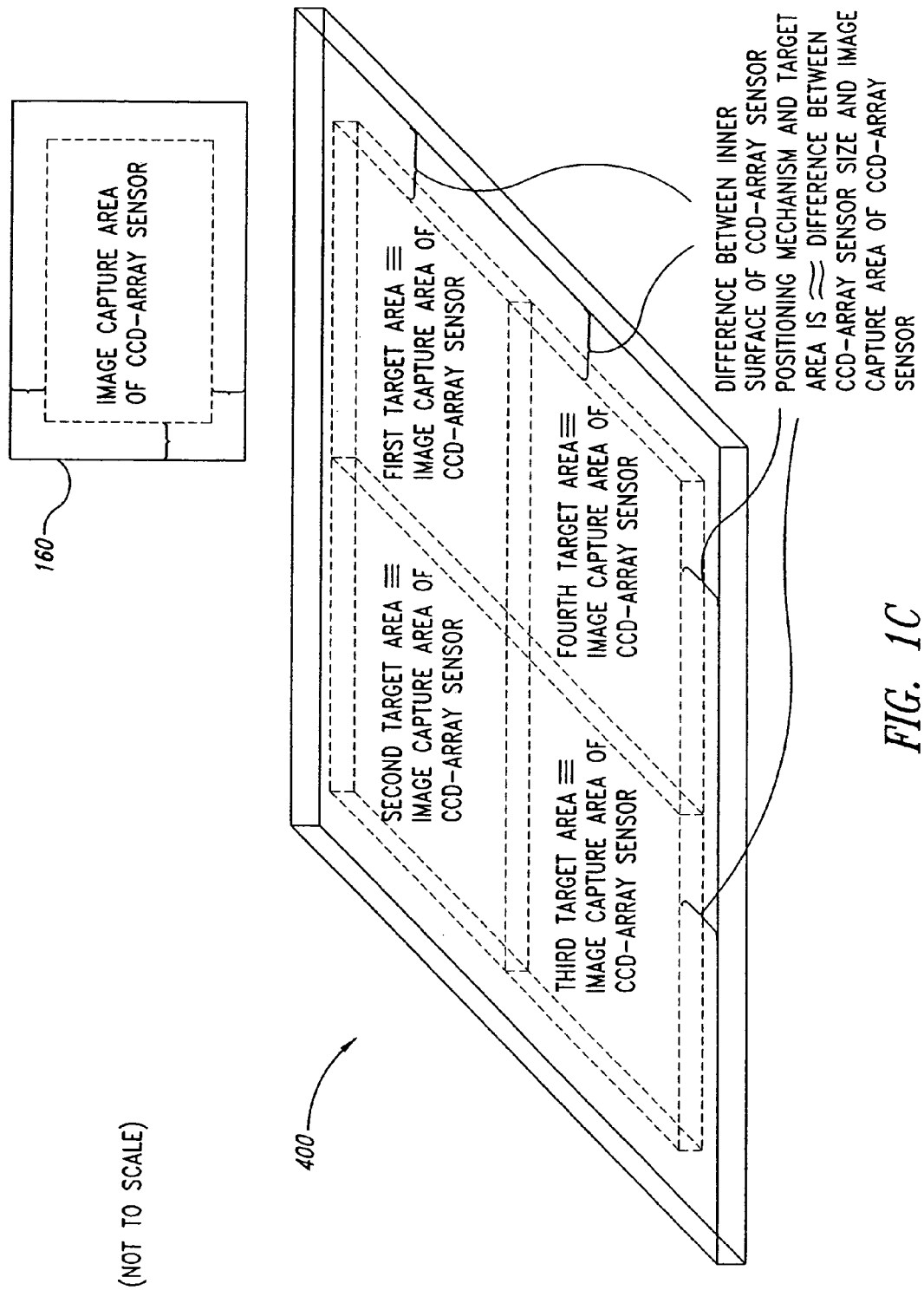
FIG. 1C shows a perspective view of how one implementation of CCD-array sensor positioning mechanism 100 is internally structured to position a CCD-array sensor to capture a radiographic image of one of four defined target areas.

As noted in relation to FIGS. 1A and 1B, CCD-array sensor positioning mechanism 100 is structured to position a CCD-array sensor (various examples of commercially available CCD-array sensors are described herein) to capture a radiographic image of at least one target area. With reference now to FIG. 1C, shown is a perspective view of how one implementation of CCD-array sensor positioning mechanism 100 is internally structured to position a CCD-array sensor to capture a radiographic image of one of four defined target areas. Shown is that CCD-array sensor positioning mechanism is internally structured such that if CCD-array sensor 160 is located at a first position, the CCD array sensor will capture a radiographic image of a first target area. Depicted is that CCD-array sensor positioning mechanism 100 is structured such that if a CCD-array sensor is located at a second position, the CCD array sensor will capture a radiographic image of a second target area. Illustrated is that CCD-array sensor positioning mechanism 100 is structured such that if a CCD-array sensor is located at a third position, the CCD array sensor will capture a radiographic image of a third target area. Shown is that CCD-array sensor positioning mechanism 100 is structured such that if a CCD-array sensor is located at a fourth position, the CCD array sensor will capture a radiographic image of a fourth target area. Also shown is that the distance between the internal surface of holder portion 400 (described in more detail below) of CCD-array sensor positioning mechanism 100 and each target area is substantially equal to the "dead space" (or inactive space) of the surface of CCD-array sensor 160, which is approximately the portion of the surface of CCD-array sensor 160, near the edge of CCD-array sensor 160, which does not record radiographic images (e.g., the dead space of the commercially available CCD-array sensors shown in FIGS. 7C, 9C, and 11C, below). Note that while four target areas are shown, it is to be understood that four areas are merely exemplary, and fewer (e.g., two) or greater (e.g., six) of such target areas can be utilized within the sprit of this disclosure, depending upon design choices of the mechanism and/or process designer.

In one implementation, the positioning of the four target areas is spatially related such that a first radiographic image recorded at the first target area, a second radiographic image recorded at the second target area, a third radiographic image recorded at the third target area, and a fourth radiographic image recorded at the fourth target area may be combined to form a composite radiographic image substantially analogous to a single radiographic image of an aggregate target area covered by the first, second, third, and fourth target areas. Note that while four target areas are described as being combined, it is to be understood that four areas are merely exemplary, and fewer (e.g., two) or greater (e.g., six) of such target areas can be utilized within the spirit of this disclosure, depending upon design choices of the mechanism and/or process designer. In one implementation, the images are processed using software present in an imaging system sold by Dexis Dental, of Palo Alto, Calif. In other implementations, Adobe Photo Deluxe and Microsoft PowerPoint have also been used to process and manipulate images.

As noted, the target areas are related such that radiographic images captured at the target areas may be combined to form a composite radiographic image substantially analogous to a single radiographic image of an aggregate target area covered by the first, second, third, and fourth target areas. In some implementations, the foregoing is achieved by having the target areas proximate to each other. Examples of target areas proximate to each other are shown in FIGS. 2A through 2B.

Figure 2A:
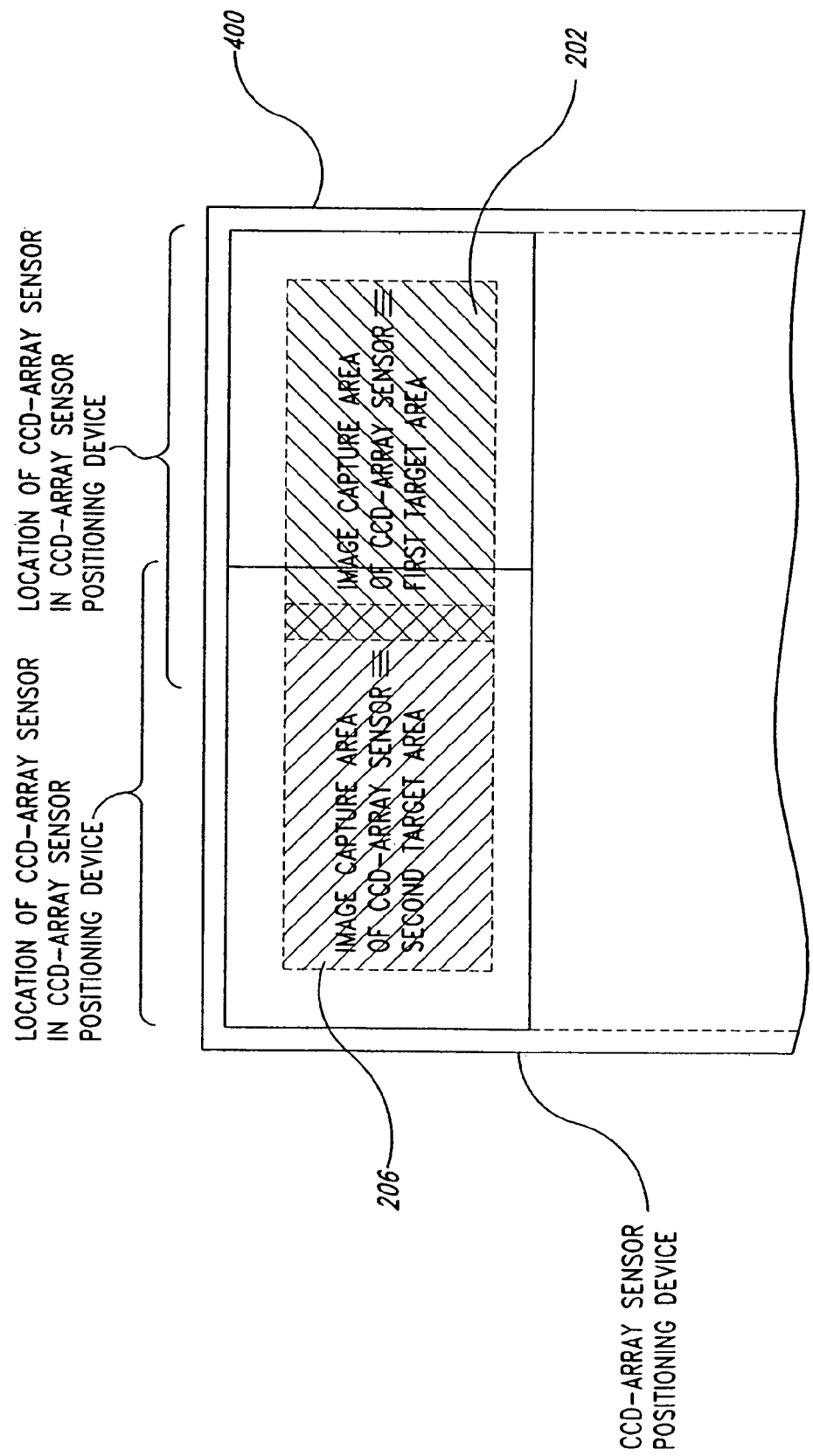
FIG. 2A illustrates an example of two target areas proximate to each other.

With reference now to FIG. 2A, illustrated is an example of two target areas proximate to each other. Shown is that the target areas are arranged such that a first radiographic image recorded in first target area 202 is slightly overlapping a second radiographic image recorded in second target area 206. Thereafter, the first image and the second radiographic image are combined utilizing image processing techniques such that they form a single radiographic image of an aggregate target area covered by first target area 202 and second target area 206. In addition, further shown is the respective positioning of CCD-array sensor 160, within holder portion of CCD-array sensor positioning mechanism 100, that is substantially necessary to capture first target area 202 and second target area 206. Note that, for sake of clarity, although only two target areas and radiographic images are described as being combined, it is to be understood that two areas are merely exemplary, and greater numbers (e.g., four, five, or six) of such target areas and radiographic images can be utilized within the spirit of this disclosure, depending upon design choices of the mechanism and/or process designer. In one implementation, the images are processed using software present in an imaging system sold by Dexis Dental, of Palo Alto, Calif. In other implementations, Adobe Photo Deluxe and Microsoft Powerpoint have also been used to process and manipulate images.

Figure 2B:
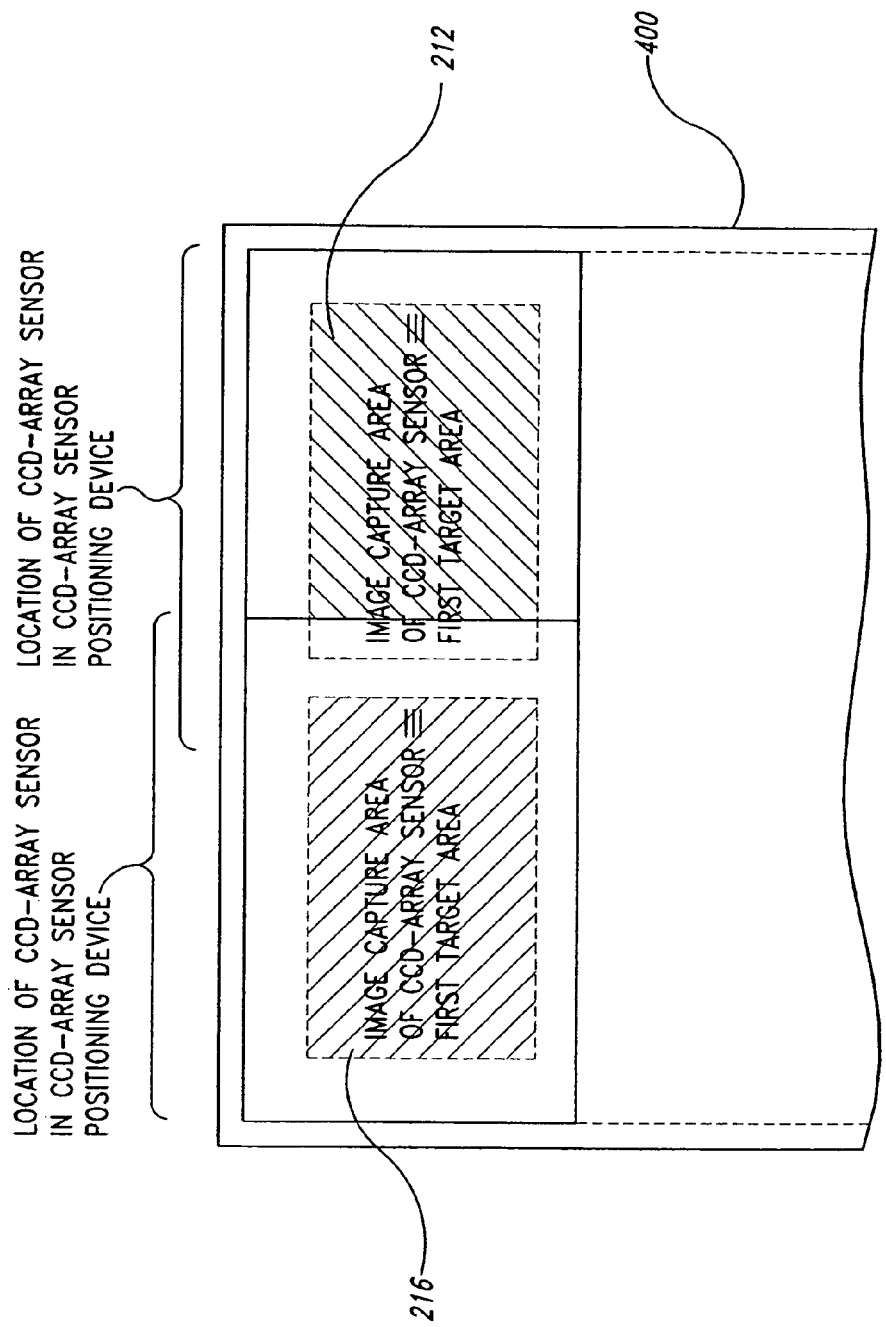
FIG. 2B illustrates an example of two target areas proximate to each other.

Referring now to FIG. 2B, illustrated is an example of two target areas proximate to each other. Shown is that the target areas are arranged such that a first radiographic image recorded in first target area 212 is substantially adjacent to a second radiographic image recorded in second target area 216. Thereafter, the first radiographic image and the second radiographic image are combined utilizing image processing techniques such that they form a single radiographic image of an aggregate target area covered by first target area 212 and second target area 216, which can then be displayed on a device such as a computer monitor. In addition, further shown is the respective positioning of CCD-array sensor 160 CCD-array sensor positioning mechanism 100 substantially necessary to capture first target area 212 and second target area 216. Note that, for sake of clarity, although only two target areas and radiographic images are described as being combined, it is to be understood that two areas are merely exemplary, and greater numbers (e.g., four, five, or six) of such target areas and radiographic images can be utilized within the spirit of this disclosure, depending upon design choices of the mechanism and/or process designer. The radiographic image can then be combined and displayed using software and/or hardware available from many commercial companies, such as such as the imaging systems sold by Dexis Dental, of Palo Alto, Calif.

With reference now to FIGS. 3A–3B, illustrated are implementations of CCD-array sensor positioning mechanism 100 wherein the CCD-array sensor positioning mechanism 100 is further structured to position the CCD-array sensor to capture the first, second, third, and forth target areas proximate to each other.

Referring now to FIG. 3A, shown is floor 300 of holder portion 400 (described in detail below) of CCD-array sensor positioning mechanism 100. Depicted is that a CCD-array sensor 160 is movable on floor 300, by sliding, between a first position at which a CCD-array sensor will capture a first target area and a second position at which CCD-array sensor 160 will capture the second target area. Depicted are pop-up hinges 310 which retract into the portion of floor 300 in the first target area and which "pop up" when CCD-array sensor 160 is moved into the second position at which CCD-array sensor 160 will capture the second target area; pop-up hinges 310 prevent the CCD-array sensor from being moved backwards into the first position and hence minimize human error.

Further illustrated are pop-up hinges 312 built into a portion of floor 300 in the second target area and which are angled such that when the CCD-array sensor 160 is moved into the second position, pop-up hinges 312 are forced to retract into floor 300; shown is that pop-up hinges 312 are positioned such that when CCD-array sensor 160 is moved from the second position to the third position which CCD-array sensor 160 will capture a third target area, pop-up hinges 312 will pop up and prevent CCD-array sensor 160 from being moved backwards into the second position and hence minimize human error. Further depicted is that CCD-array sensor positioning mechanism 100 is structured such that CCD-array sensor 160 is movable, by sliding, between the second position at which the CCD-array sensor will capture a second target area and a third position which the CCD-array sensor will capture a third target area.

Further shown are pop-up hinges 314 built into a portion of floor 300 in the third target area and which are angled such that when the CCD-array sensor 160 is moved into the third position, pop-up hinges 314 are forced to retract into floor 300; shown is that pop-up hinges 314 are positioned such that when CCD-array sensor 160 is moved from the third position to a fourth position which CCD-array sensor 160 will capture a fourth target area, pop-up hinges 314 will pop up and prevent CCD-array sensor 160 from being moved backwards into the third position and hence minimize human error. Further illustrated is that CCD-array sensor positioning mechanism 100 is structured such that CCD-array sensor 160 is movable, by sliding, between the third position at which the CCD-array sensor will capture a third target area the fourth position which the CCD-array sensor will capture a fourth target area. Pop-up hinges 310, 312, and 314 are present so that the likelihood of the human operator moving the sensor to the wrong target area (e.g., moving the sensor to take a image of a target already captured) in the wrong sequence is minimized. For sake of clarity, rotation axis of pop-up hinges 310, 312, and 314 are denoted by reference numeral 318. It is to be understood that the portion of pop-up hinges that "pops up" is the portion opposite rotation axis 318.

With reference now to FIG. 3B, shown is a cut-away side plan view of CCD-array sensor positioning device 100, wherein shown is an exemplar of pop-up hinges 310 (and, by extension pop-up hinges 312 and 314). It is to be understood that pop-up hinges 310, 312, and 314 are substantially structurally the same, and the three sets of reference numerals used to describe them in relation to FIG. 3A are used to account for the pop-up hinges 310, 312, and 314 different orientations in target areas one, two, and three, respectively. Those skilled in the art will recognize will recognize that the pop-up hinges depicted and described are merely exemplary of the type of devices which will allow motion of CCD-array sensor 160 in one direction through target areas one, two, three, and four.

In one implementation, CCD-array sensor positioning mechanism 100 is composed of three constituent parts: a holder device portion, a stabilization device portion, and a positioning device portion (which perform function somewhat analogous to the functions performed by pop-up hinges 310, 312, and 314 of FIGS. 3A and 3B). It is to be understood that the foregoing-noted constituent parts are present in one implementation, and it is not necessary that all such constituent parts be present in every implementation. Following are set forth and described implementations of the foregoing-described constituent parts of one implementation of CCD-array sensor positioning mechanism 100. Also described is how such implementations can be used with various commercially available CCD-array sensors.

Figure 4A:
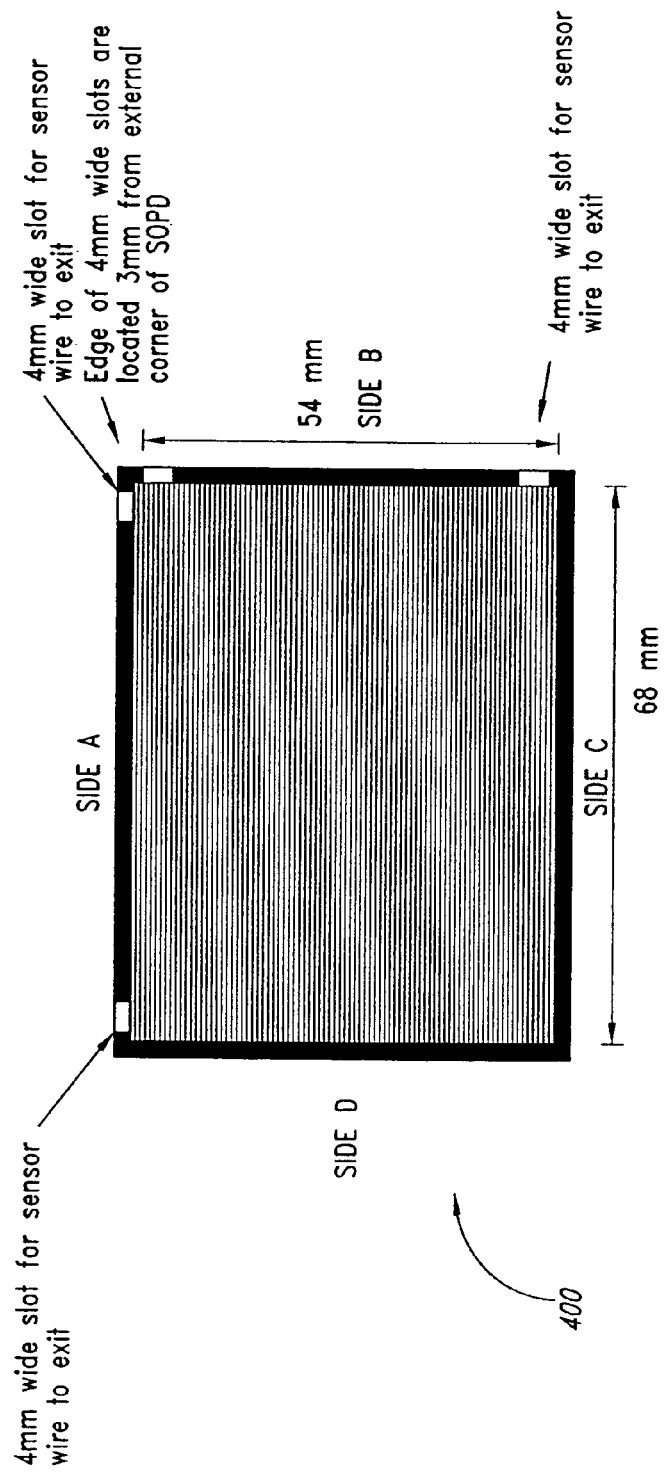
FIG. 4A shows a top plan view of holder portion 400 of CCD-array sensor positioning mechanism 100.

Referring now to FIG. 4A, shown is a top plan view of holder portion 400 of CCD-array sensor positioning mechanism 100. Depicted is that the internal dimensions of holder portion 400 are 68 mm×54 mm. The internal depth (not shown) of holder portion 400 is 15 mm (deep enough to hold the thickest commercially available CCD-array sensor, discussed below, when sandwiched with stabilization portion 500, discussed below). Illustrated is that side A (one of the 68 mm sides) has two 4 mm slots to allow a sensor wire of a CCD-array sensor to exit when the CCD-array sensor is placed in holder portion 400 in order to capture a target area analogous to one of the target areas discussed above. Shown is that side B (one of the 54 mm sides) has two 4 mm slots to allow the sensor wire of a CCD-array sensor to exit when a CCD-array sensor is placed in holder portion 400 in order to capture a target area analogous to one of the target areas discussed above.

Figure 4B:
FIG. 4B depicted is a cutaway side plan view of side A of holder portion 400.

With reference now to FIG. 4B, depicted is a cutaway side plan view of side A of holder portion 400. Illustrated is that holder portion 400 has an external height of 16.5 mm, and internal depth of 15 mm, and an external length of 70 mm.

Figure 4C:
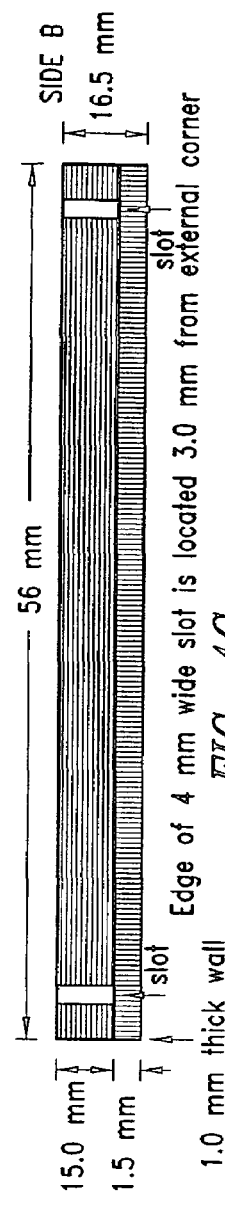
FIG. 4C depicts a cutaway side plan view of side B of holder portion 400.

With reference now to FIG. 4C, depicted is a cutaway side plan view of side B of holder portion 400. Illustrated is that holder portion 400 has an external height of 16.5 mm, an internal depth of 15 mm, and an external length of 56 mm.

Figure 4D:
FIG. 4D depicts a cutaway side plan view of side C of holder portion 400. Illustrated is that holder portion 400 has an external height of 16.5 mm, and internal dept of 15 mm, and an external length of 70 mm.

With reference now to FIG. 4D, depicted is a cutaway side plan view of side C of holder portion 400. Illustrated is that holder portion 400 has an external height of 16.5 mm, and internal dept of 15 mm, and an external length of 70 mm.

Figure 4E:
FIG. 4E depicts a cutaway side plan view of side D of holder portion 400.

With reference now to FIG. 4E, depicted is a cutaway side plan view of side D of holder portion 400. Illustrated is that holder portion 400 has an external height of 16.5 mm, and internal depth of 15 mm, and an external length of 56 mm.

Certain commercially available CCD-array sensors, described below, have external shells which are not entirely flat. For example, some have rounded shells. As a consequence of this, such CCD-array sensors tend to rock back and forth when placed in holder portion 400, which can cause sub-optimal capturing of images. In some embodiments, holder portion 400 is machined to accommodate the rounded shells of certain CCD-array sensors, thereby rendering such rounded shells stable. However, in another embodiment, CCD-array sensor positioning device 100 includes a stabilization portion which is such that it "sandwiches" down onto holder portion 400 in a way such that an inner surface of the stabilization portion impinges upon the surface of a CCD-array sensor in holder portion 400 such that a CCD-array sensor is held stable in holder portion 400.

Figure 5A:
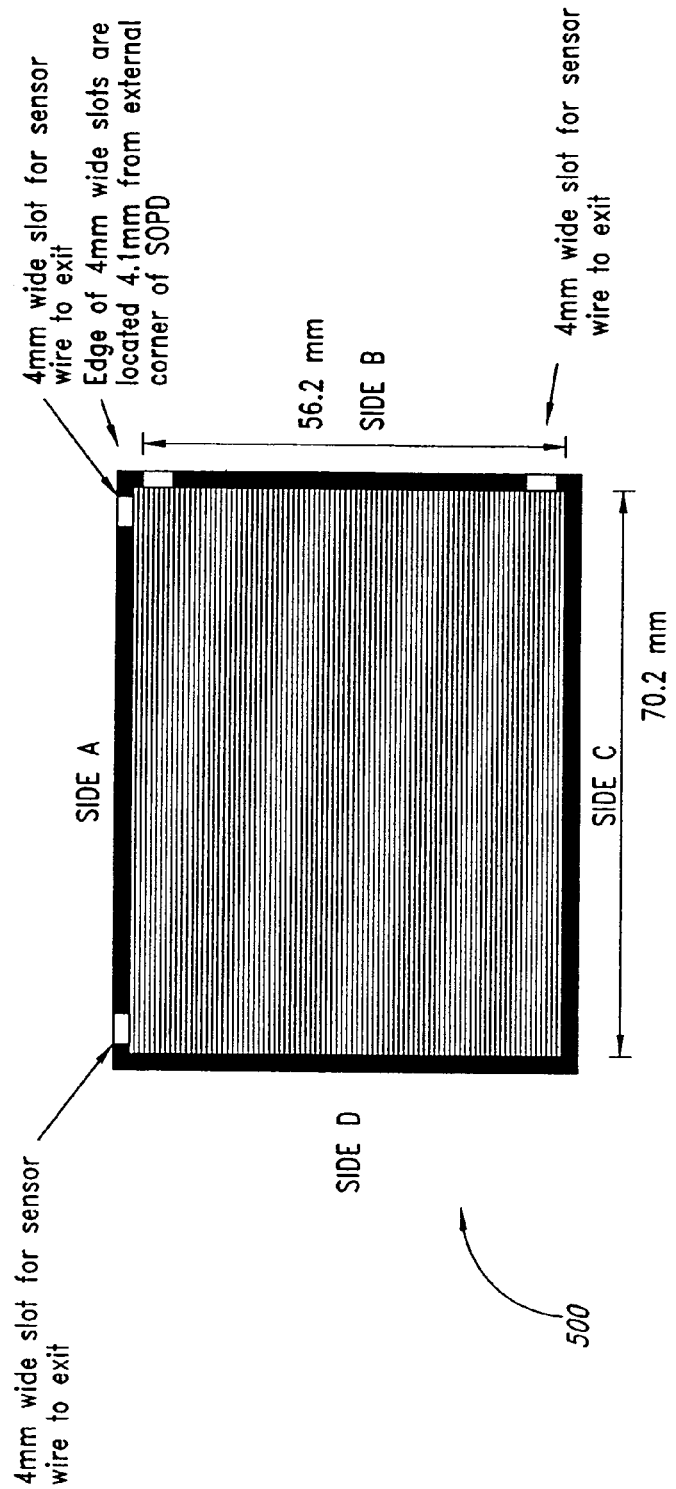
FIG. 5A shows a top plan view of stabilization portion 500 of CCD-array sensor positioning mechanism 100.

With reference now to FIG. 5A, shown is a top plan view of stabilization portion 500 of CCD-array sensor positioning mechanism 100. Stabilization portion 500 is designed to sandwich onto holder portion 400. Accordingly, depicted is that the internal dimensions of stabilization portion 500 are 70.2 mm×56.2 mm (just big enough to fit over holder portion 400, with a small bit of play, or slack). The internal depth (not shown) of stabilization portion 500 is 15 mm (deep enough to hold the thickest commercially available CCD-array sensor, discussed below, when stabilization portion 500 is sandwiched down onto holder portion 400). Illustrated is that side A (one of the 70.2 mm sides) has two 4 mm slots to allow a sensor wire of a CCD-array sensor to exit when the CCD-array sensor is placed in holder portion 400 in order to capture a target area analogous to one of the target areas discussed above; the 4 mm slots of side A are positioned such that when stabilization portion 500 is sandwiched onto holder portion 400, the 4 mm slots of side A of stabilization portion 500 and side A of holder portion 400 are substantially aligned. Shown is that side B (one of the 56.2 mm sides) has two 4 mm slots to allow the sensor wire of a CCD-array sensor to exit when a CCD-array sensor is placed in holder portion 400 in order to capture a target area analogous to one of the target areas discussed above; the 4 mm slots of side B are positioned such that when stabilization portion 500 is sandwiched onto holder portion 400, the 4 mm slots of side B of stabilization portion 500 and side holder portion 400 are substantially aligned.

With reference now to FIG. 5B, depicted is a cutaway side plan view of side A of stabilization portion 500. Illustrated is that stabilization portion 500 has an external height of 16.5 mm, and internal depth of 15 mm, and an external length of 71.2 mm. The slots shown in side A of stabilization portion 500 are such that they align with the slots of side A of holder portion 400 when stabilization portion 500 is sandwiched onto holder portion 400.

With reference now to FIG. 5C, depicted is a cutaway side plan view of side B of stabilization portion 500. Illustrated is that stabilization portion 500 has an external height of 16.5 mm, an internal depth of 15 mm, and an external length of 57.2 mm. The slots shown in side B of stabilization portion 500 are such that they align with the slots of side B of holder portion 400 when stabilization portion 500 is sandwiched onto holder portion 400.

With reference now to FIG. 5D, depicted is a cutaway side plan view of side C of stabilization portion 500. Illustrated is that stabilization portion 500 has an external height of 16.5 mm, and internal dept of 15 mm, and an external length of 71.2 mm.

With reference now to FIG. 5E, depicted is a cutaway side plan view of side D of stabilization portion 500. Illustrated is that stabilization portion 500 has an external height of 16.5 mm, and internal depth of 15 mm, and an external length of 57.2 mm.

Many implementations exist whereby holder portion 400 (and stabilization portion 500, should stabilization be necessary) of CCD-array sensor positioning mechanism 100 can be utilized with implementations of positioning devices keyed to several commercially available CCD-array sensors. A few of these implementations will now be described.

Figure 6A:
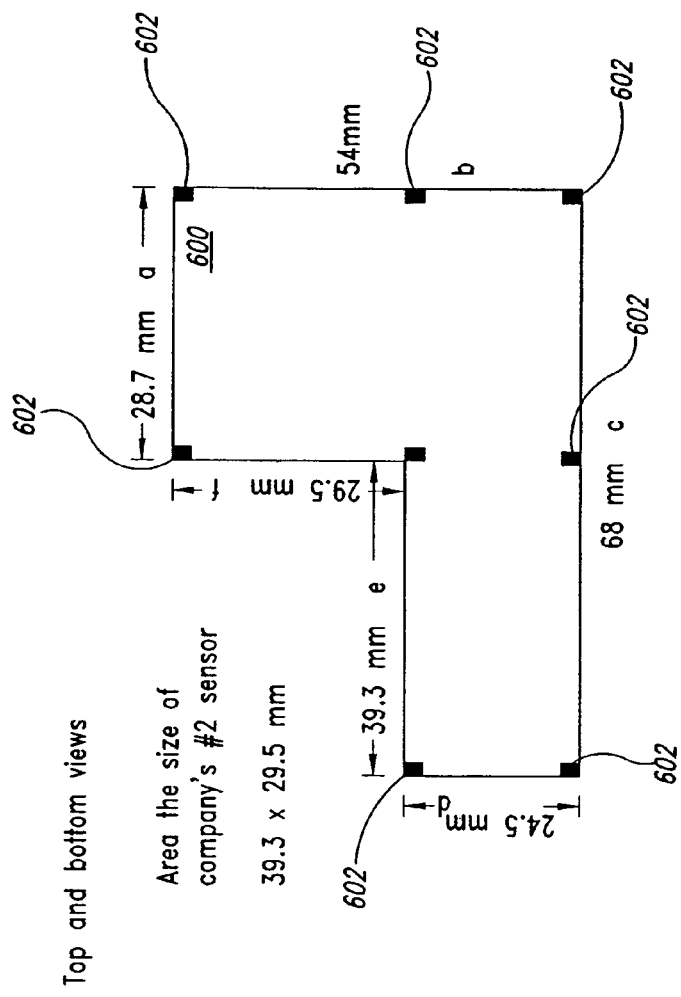
FIG. 6A illustrates a top plan view of solid positioning block 600 for a #2 CCD-array sensor available from New Image/Dentsply and Dexis Companies.
Figure 6B:
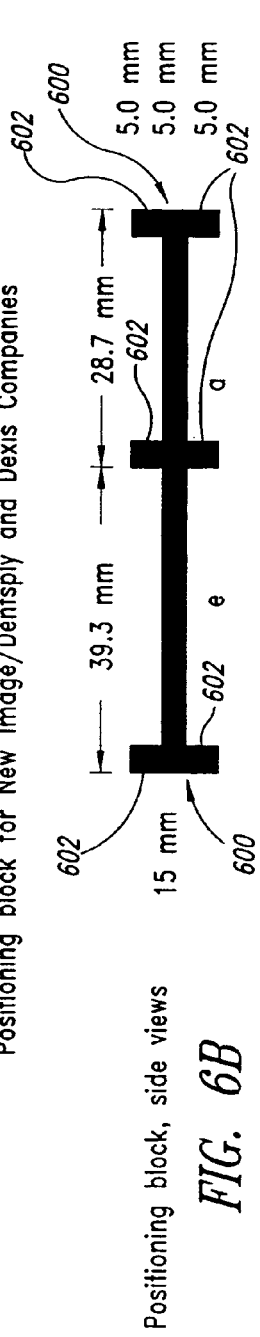
FIGS. 6B–6E depict side plane views of solid positioning block 600.
Figure 6C:
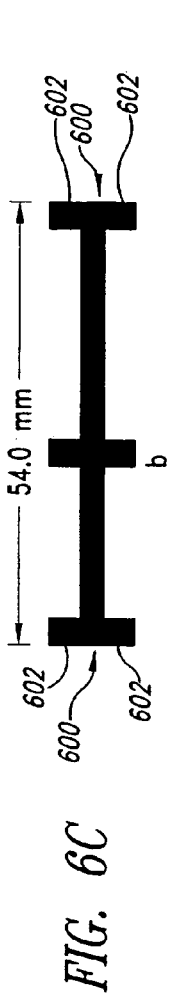
Figure 6D:
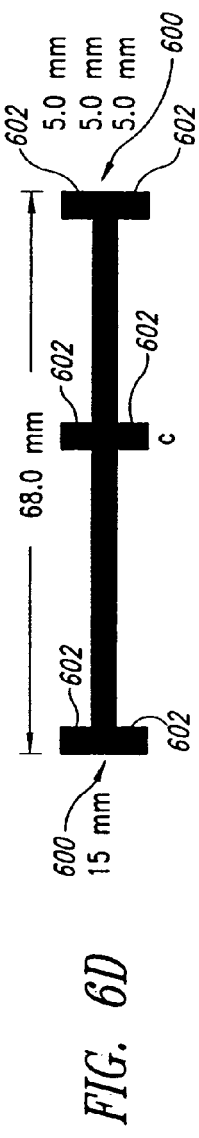
Figure 6E:
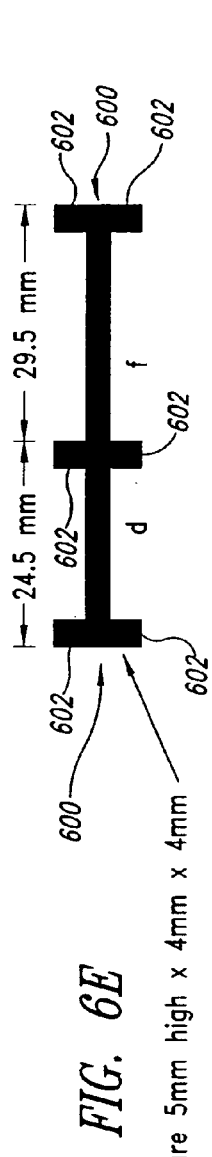

Referring now to FIG. 6A, illustrated is a top plan view of solid positioning block 600 for a #2 CCD-array sensor available from New Image/Dentsply and Dexis Companies. Shown is that positioning block 600 has dimensions such that positioning block 600 will fit snugly within the interior dimensions of holder portion 400 and then accept a 39.3×29.5 mm sensor into the space of holder portion 400 such that a radiographic image of a first target area may be obtained. Notice that positioning block 600 can be flipped along its vertical and horizontal axis such that a CCD-array sensor can be repeatedly positioned within the interior of holder portion 400 such that radiographic images from four different target areas can be captured. Shown is that eight legs (or supports) 602 extend through solid positioning device 600.

With reference now to FIGS. 6B–6E, depicted are side plan views of solid positioning block 600. Depicted are the dimensions and locations of the eight legs (or supports) 602 which extend through solid positioning device 600. Legs 602 provide support such that a cord of a Dexis #2 CCD array sensor (e.g., see FIGS. 7B, 7D) will not become trapped but can move easily under positioning device 600. Other embodiments are contemplated wherein a lip, or ledge, is placed around the interior of holder portion 400 where the lip essentially supports a legless implementation of positioning block 600, the lip essentially performing the functions performed by legs 602 in the implementation of positioning block 600 shown in FIGS. 6A–6E.

Figure 7A:
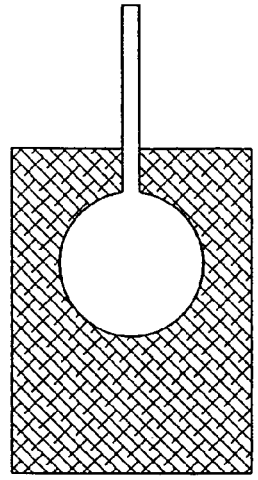
FIGS. 7A–D respectively illustrate views of either a Dexis or a Dentsply/New Image #2 CCD-array sensor (the Dexis and Dentsply/New Image #2 sensors are substantially the same size) which can be utilized with solid positioning block 600 to obtain images (e.g., occlusal images).
Figure 7B:
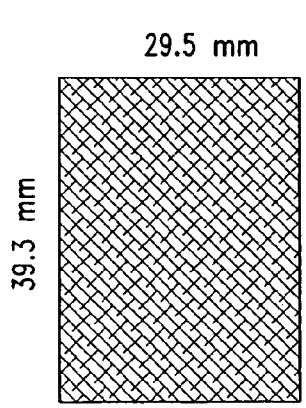
Figure 7C:
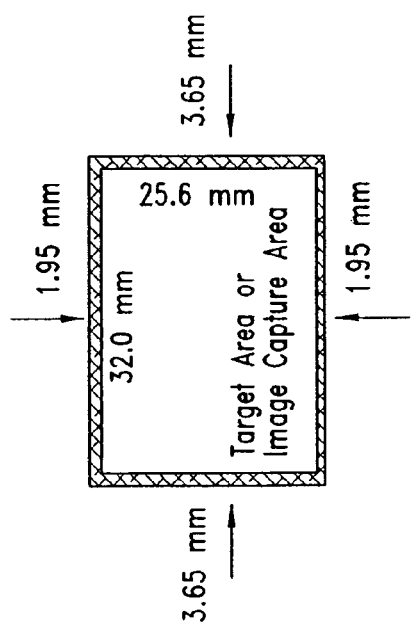
Figure 7D:
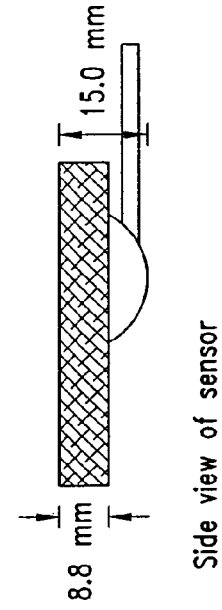

Referring now to FIGS. 7A–D, respectively illustrated are views of either a Dexis or a Dentsply/New Image #2 CCD-array sensor (the Dexis and Dentsply/New Image #2 sensors are substantially the same size) which can be utilized with solid positioning block 600 to obtain images (e.g., occlusal images). FIG. 7A shows a top plan view of a Dexis #2 CCD-array sensor having dimensions 39.3 mm×29.5 mm. FIG. 7B shows a bottom plan view of a Dexis #2 CCD-array sensor showing how a cord connects to the sensor. FIG. 7C shows a top plan view of a target area, at which a radiographic image can be captured, of a Dexis #2 CCD-array sensor having dimensions 39.3 mm×29.5 mm, where the target area (or image capture area) is shown to be 32 mm×25.6 mm. FIG. 7D shows a side view of a Dexis #2 sensor; notice that where the cord connects to the sensor gives rise to a rounded area, which is one reason why stabilization portion 500, described above, is sometimes necessary to stabilize sensors held in CCD-array sensor positioning mechanism 100.

In addition to the forgoing described implementations for the Dexis (or Dentsply/New Image) #2 CCD-array sensor, other implementations for other commercially available CCD-array sensors have been devised. These implementations are described below.

Figure 8A:
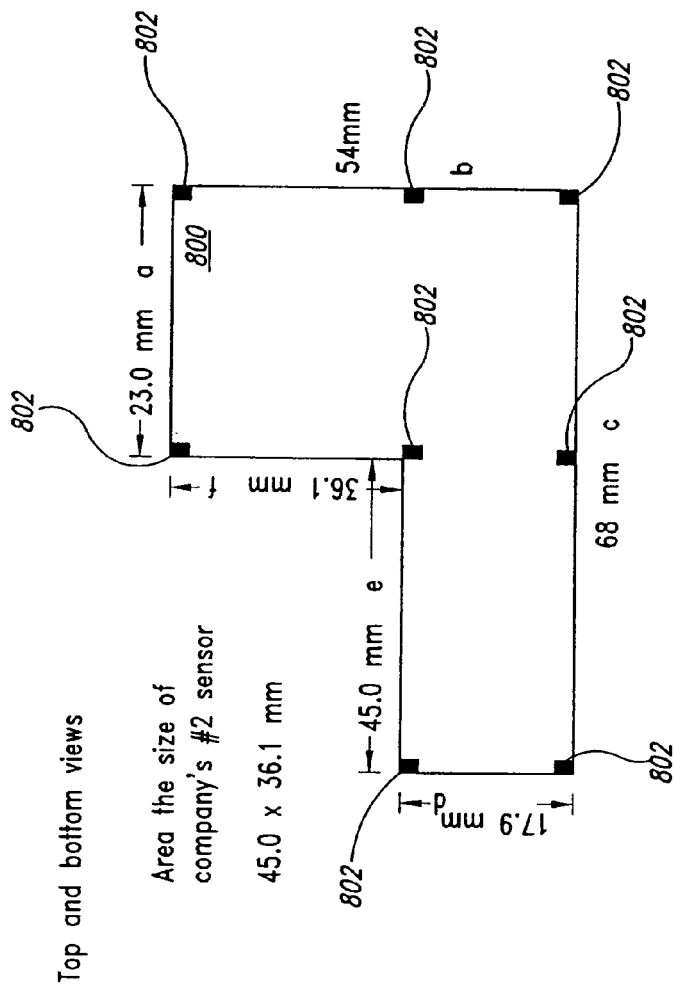
FIG. 8A illustrates a top plan view of solid positioning block 800 for a #2 CCD-array sensor available from Trophy Company.

With reference now to FIG. 8A, illustrated is a top plan view of solid positioning block 800 for a #2 CCD-array sensor available from Trophy Company. Shown is that positioning block 800 has dimensions such that positioning block 800 will fit snugly within the interior dimensions of holder portion 400 and then accept a 45×36.1 mm sensor into the space of holder portion 400 such that a radiographic image of a first target area may be obtained. Notice that positioning block 800 can be flipped along its vertical and horizontal axis such that a CCD-array sensor can be repeatedly positioned within the interior of holder portion 400 such that radiographic images from four different target areas can be captured. Shown is that eight legs (or supports) 802 extend through solid positioning device 800.

With reference now to FIGS. 8B–8E, depicted are side plan views of solid positioning block 800. Depicted are the dimensions and locations of the eight legs (or supports) 802 which extend through solid positioning device 800. Legs 802 provide support such that a cord of a Trophy #2 CCD array sensor (e.g., see FIGS. 9B, 9D) will not become trapped but can move easily under positioning device 800. Other embodiments are contemplated wherein a lip, or ledge, is placed around the interior of holder portion 400 where the lip essentially supports a legless implementation of positioning block 800, the lip essentially performing the functions performed by legs 802 in the implementation of positioning block 800 shown in FIGS. 8A–8E.

Figure 9A:
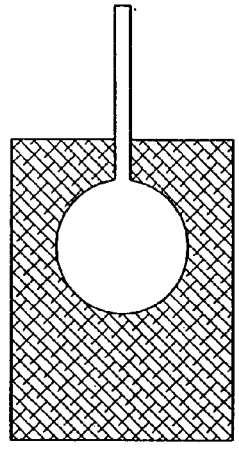
FIGS. 9A–D respectively illustrate views of a Trophy #2 CCD-array sensor which can be utilized with solid positioning block 800 to obtain images (e.g., occlusal images).
Figure 9B:
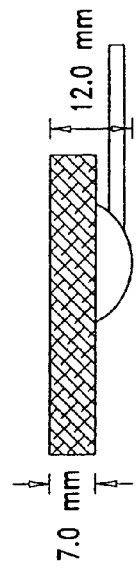
Figure 9C:
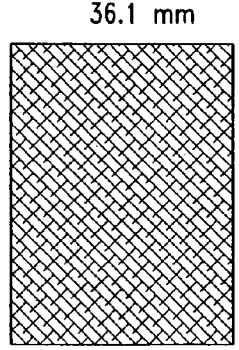
Figure 9D:
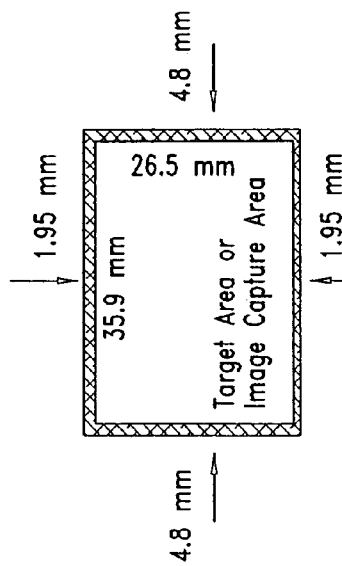

Referring now to FIGS. 9A–D, respectively illustrated are views of a Trophy #2 CCD-array sensor which can be utilized with solid positioning block 800 to obtain images (e.g., occlusal images). FIG. 9A shows a top plan view of a Trophy #2 CCD-array sensor having dimensions 45 mm×36.1 mm. FIG. 9B shows a bottom plan view of a Trophy #2 CCD-array sensor showing where a cord connects to the sensor. FIG. 9C shows a top plan view of a target area, at which a radiographic image can be captured, of a Trophy #2 CCD-array sensor having dimensions 45 mm×36.1 mm, where the target area (or image capture area) is shown to be 35.9 mm×26.5 mm. FIG. 9D shows a side view of a Trophy #2 sensor; notice that where the cord connects to the sensor gives rise to a rounded area, which is one reason why stabilization portion 500, described above, is sometimes necessary to stabilize the sensors held in CCD-array sensor positioning mechanism 100.

Figure 10A:
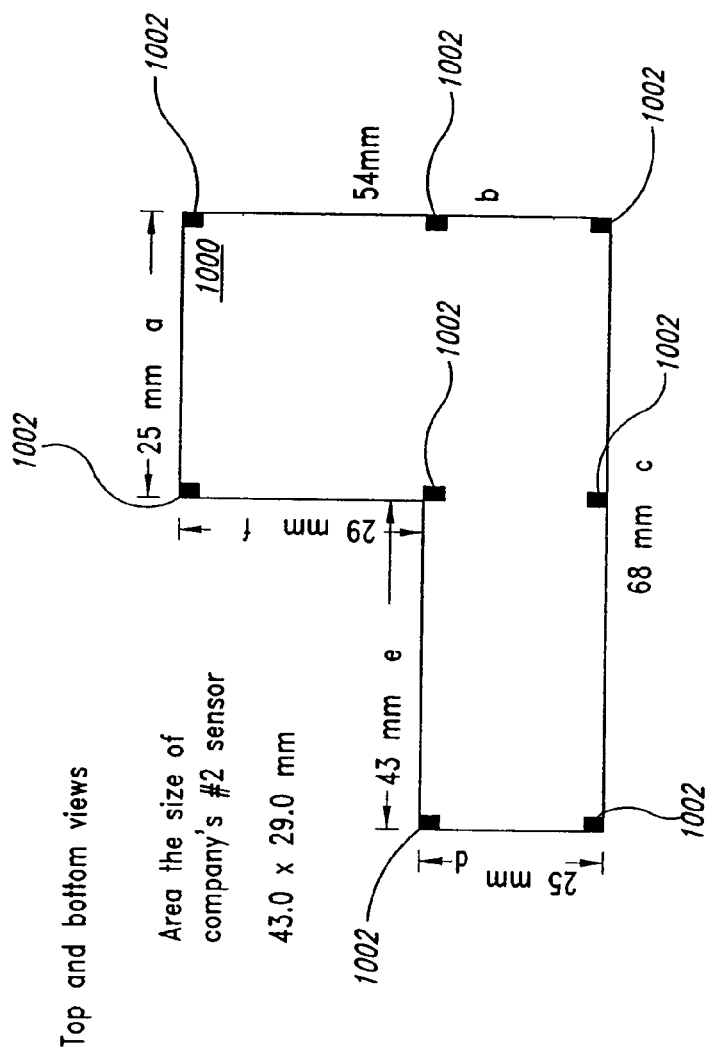
FIG. 10A illustrates a top plan view of solid positioning block 1000 for a #2 CCD-array sensor available from Shick Company.
Figure 10B:
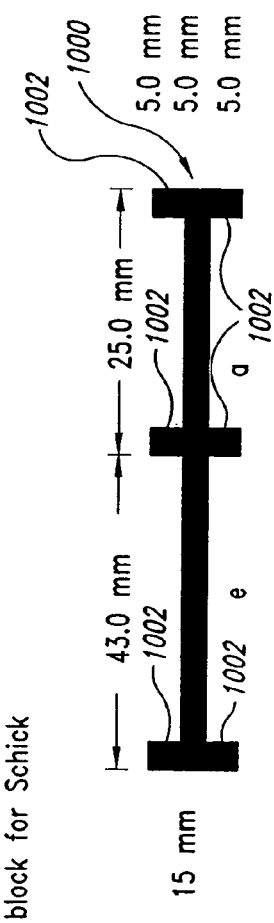
FIGS. 10B–10E depict side plane views of solid positioning block 1000.
Figure 10C:
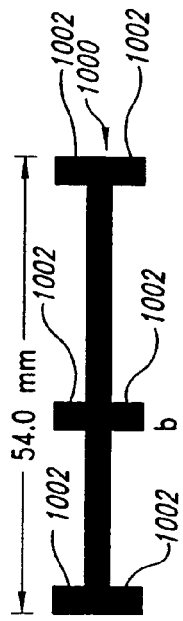
Figure 10D:
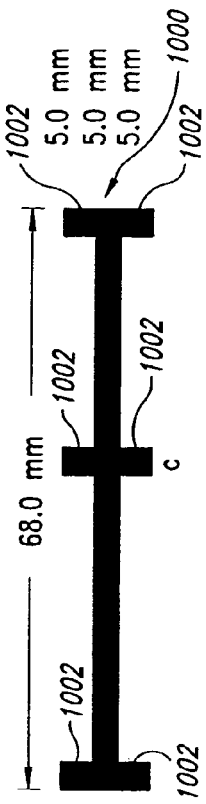
Figure 10E:
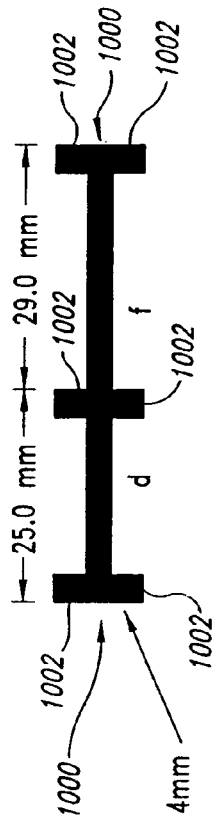

With reference now to FIG. 10A, illustrated is a top plan view of solid positioning block 1000 for a #2 CCD-array sensor available from Shick Company. Shown is that positioning block 1000 has dimensions such that positioning block 1000 will fit snugly within the interior dimensions of holder portion 400 and then accept a 43×29 mm sensor into the space of holder portion 400 such that a radiographic image of a first target area may be obtained. Notice that positioning block 1000 can be flipped along its vertical and horizontal axis such that a CCD-array sensor can be repeatedly positioned within the interior of holder portion 400 such that radiographic images from four different target areas can be captured. Shown is that eight legs (or supports) 1002 extend through solid positioning device 1000.

With reference now to FIGS. 10B–10E, depicted are side plan views of solid positioning block 1000. Depicted are the dimensions and locations of the eight legs (or supports) 102 which extend through solid positioning device 800. Legs 1002 provide support such that a cord of a Trophy #2 CCD array sensor (e.g., see FIGS. 11B, 11D) will not become trapped but can move easily under positioning device 1000. Other embodiments are contemplated wherein a lip, or ledge, is placed around the interior of holder portion 400 where the lip essentially supports a legless implementation of positioning block 1000, the lip essentially performing the functions performed by legs 1002 in the implementation of positioning block 1000 shown in FIGS. 10A–10E.

Figure 11A:
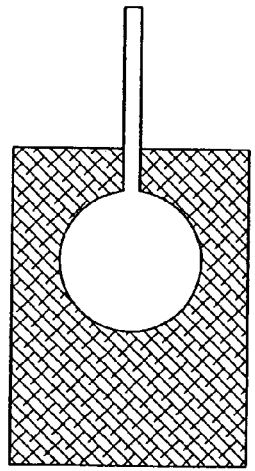
FIGS. 11A–D respectively illustrate views of a Shick #2 CCD-array sensor which can be utilized with solid positioning block 1000 to obtain images (e.g., occlusal images).
Figure 11B:
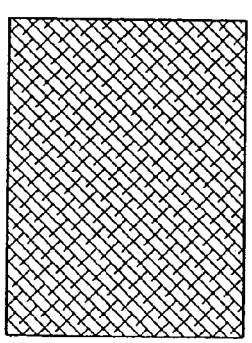
Figure 11D:
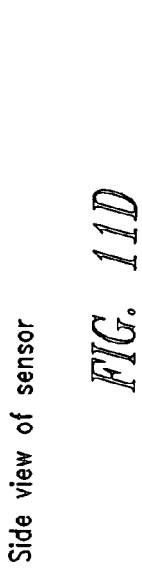
Figure 11C:
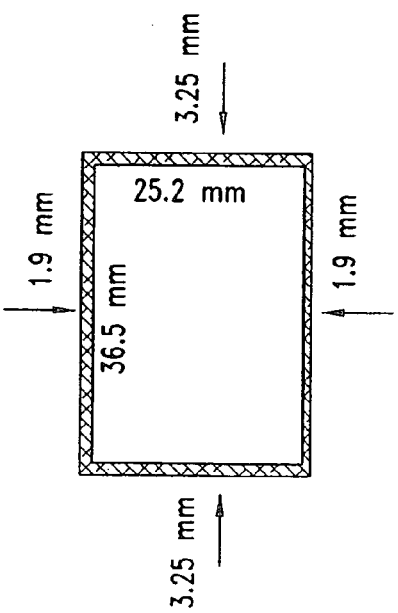

Referring now to FIGS. 11A–D, respectively illustrated are views of a Shick #2 CCD-array sensor which can be utilized with solid positioning block 1000 to obtain images (e.g., occlusal images). FIG. 11A shows a top plan view of a Shick #2 CCD-array sensor having dimensions 43 mm×29 mm. FIG. 11B shows a bottom plan view of a Shick #2 CCD-array sensor showing where a cord connects to the sensor. FIG. 11C shows a top plan view of a target area, at which a radiographic image can be captured, of a Shick #2 CCD-array sensor having dimensions 43×29 mm, where the target area (or image capture area) is shown to be 36.56 mm×25.2 mm. FIG. 11D shows a side plan view of a Shick #2 sensor; notice that where the cord connects to the sensor gives rise to a rounded area, which is one reason why stabilization portion 500, described above, is sometimes necessary to stabilize the sensors held in CCD-array sensor positioning mechanism 100.

Once holder portion 400 and stabilization portion 500 have been sandwiched together, the composite structure can be used to capture radiographic images in fashions such as were shown in FIGS. 1A and 1B, above. Insofar as it is desired to take multiple radiographic images of target areas substantially proximate to each other, it is necessary to somehow stabilize CCD-array sensor positioning mechanism 100 in a patient's mouth such that the multiple images are taken in substantially the same location relative to each other.

In one implementation, the multiple images are taken in substantially the same location relative to each other by affixing a portion of CCD-array sensor positioning mechanism 100 in the mouth. That is, in one implementation the dentist checks for the fit of stabilization portion 500 on the patient's maxillary arch, with the CCD-array sensor positioning mechanism 100 oriented such that the slot for the sensor wire will exit toward the anterior of the patient's mouth through the slots on either side A or side B. Thereafter, the dentist injects a flexible fast set Polyvinysiloxane (PVS)—a substance typically used to take dental impressions—along the maxillary or mandibular occlusal surface, places stabilization portion 500 on the arch, and holds stabilization portion 500 steady with finger pressure until the PVS has set. Once the PVS has set, the dentist then removes and then removes stabilization portion 500 from the patient's mouth.

Thereafter, since the PVS essentially has a dental impression of the patient's maxillary or mandibular arch, stabilization portion 500 can be removed from and then subsequently replaced to the patient's maxillary arch, and the dental impression taken will insure that the CCD-array sensor positioning mechanism 100 returns to a repeatable position in the mouth. Consequently, once the PVS impression has been obtained, CCD-array sensor positioning mechanism 100 can be inserted and removed from the mouth the number of times necessary to capture the number of radiographic images of the target areas necessary to construct a composite image of interest. A similar set of operations is also done to obtain a mandibular view, but holder portion 400 will be the portion to which PVS is applied and used to take a dental impression of the patient's mandibular arch.

In one implementation, the ability to obtain the foregoing-described dental impressions is enhanced by the external structures of holder device 400 and stabilization device 500. Implementations of such external structures will now be described.

Figure 12:
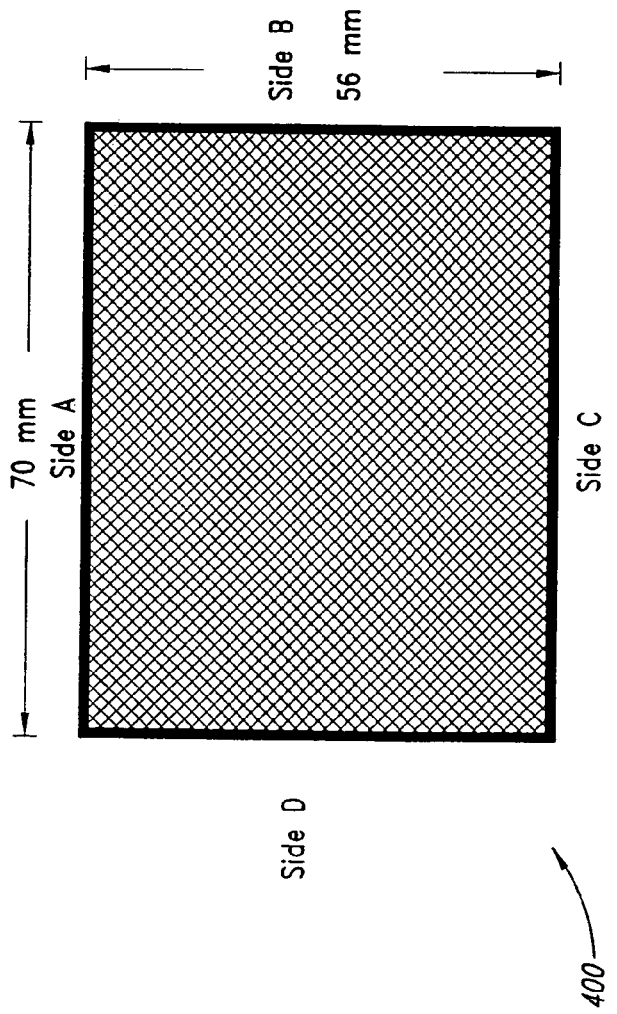
FIG. 12 shows a bottom plan view of holder portion 400 of CCD-array sensor positioning mechanism 100.

Referring now to FIG. 12, shown is a bottom plan view of holder portion 400 of CCD-array sensor positioning mechanism 100. Depicted is that the external structure of the bottom of holder portion 400 is formed to have a grid structure wherein each grid element is 2 mm wide, 2 mm long, and 1 mm deep. This grid structure allows the PVS to adhere well to holder portion 400.

Figure 13:
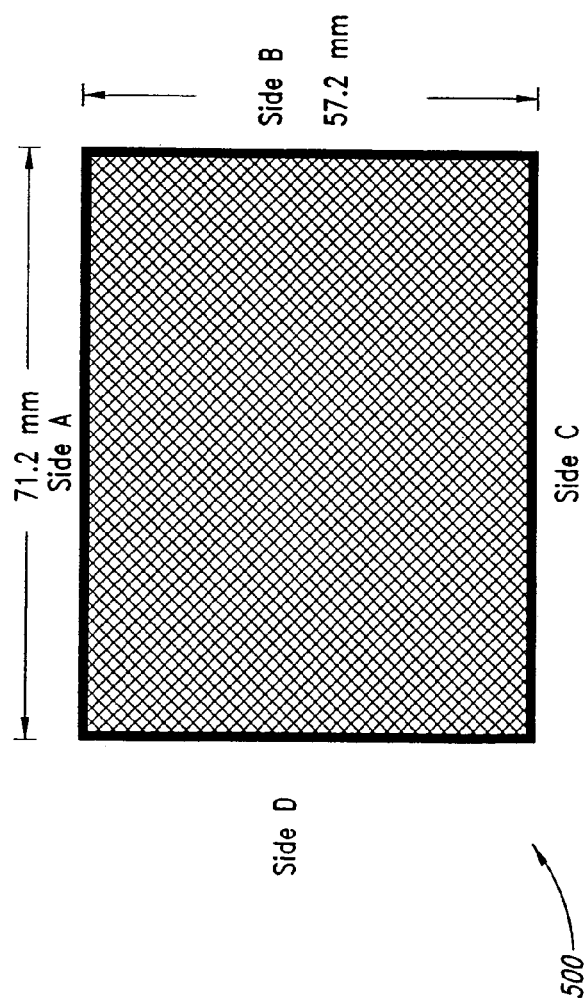
FIG. 13 depicts a top plan view of stabilization portion 500 of CCD-array sensor positioning mechanism 100.

With reference now to FIG. 13, depicted is a top plan view of stabilization portion 500 of CCD-array sensor positioning mechanism 100. Depicted is that the external structure of the top of stabilization portion 500 is formed to have a grid structure wherein each grid element is 2 mm wide, 2 mm long, and 1 mm deep. This grid structure allows the PVS to adhere well to stabilization portion 500.

With reference now to FIGS. 14A–D, respectively shown are four different examples of how a CCD-array sensor may be placed in CCD-array sensor device positioning mechanism 100 to capture a radiographic image of four different respectively proximate target areas. The four different target areas are not explicitly shown, but each target area is to be understood to equate to the image capture area of the CCD-array sensor such as was described for the CCD-array sensors shown in FIGS. 7C, 9C, and 11C.

Referring now to FIG. 15, shown is an example of how the respective images captured at the respectively proximate target areas of 14A–D can overlap. The overlapping images can then be processed with image processing software as described above in order to create a composite image of the aggregate area covered by the respective target areas.

With reference now to FIGS. 16A–16D, respectively shown are four different examples of how a CCD-array sensor may be placed in CCD-array sensor device positioning mechanism 100 to capture a radiographic image of four different respectively proximate target areas. The four different target areas are not explicitly shown, but each target area is to be understood to equate to the image capture area of the CCD-array sensor such as was described for the CCD-array sensors shown in FIGS. 7C, 9C, and 11C.

Referring now to FIG. 17, shown is an example of how the respective images captured at the respectively proximate target areas of 16A–16D can overlap. The overlapping images can then be processed with image processing software as described above in order to create a composite image of the aggregate area covered by the respective target areas.

Those skilled in the art will recognize that the state of the art has progressed to the point where there is little distinction left between hardware and software implementations of aspects of systems; the use of hardware or software is generally a design choice representing cost vs. efficiency tradeoffs. The foregoing detailed description has set forth various embodiments of the devices and/or processes via the use of block diagrams, flowcharts, and examples. Insofar as such block diagrams, flowcharts, and examples contain one or more functions and/or operations, it will be understood as notorious by those within the art that each function and/or operation within such block diagrams, flowcharts, or examples can be implemented, individually and/or collectively, by a wide range of hardware, software, firmware, or any combination thereof. In one embodiment, the devices and/or processes described herein may be implemented via Application Specific Integrated Circuits (ASICs). However, those skilled in the art will recognize that the embodiments disclosed herein, in whole or in part, can be equivalently implemented in standard Integrated Circuits, as a computer program running on a computer, as firmware, or as virtually any combination thereof and that designing the circuitry and/or writing the code for the software or firmware would be well within the skill of one of ordinary skill in the art in light of this disclosure. In addition, those skilled in the art will appreciate that the mechanisms of the devices and/or processes described herein are capable of being distributed as a program product in a variety of forms, and that an illustrative embodiment of the devices and/or processes described herein applies equally regardless of the particular type of signal bearing media used to actually carry out the distribution. Examples of a signal bearing media include but are not limited to the following: recordable type media such as floppy disks, hard disk drives, CD ROMs, digital tape, and transmission type media such as digital and analogue communication links using TDM or IP based communication links (e.g., packet links).

In a general sense, those skilled in the art will recognize that the various embodiments described herein which can be implemented, individually and/or collectively, by a wide range of hardware, software, firmware, or any combination thereof can be viewed as being composed of various types of "electrical circuitry." Consequently, as used herein "electrical circuitry" includes but is not limited to electrical circuitry having at least one discrete electrical circuit, electrical circuitry having at least one integrated circuit, electrical circuitry having at least one application specific integrated circuit, electrical circuitry forming a general purpose computing device configurable by a computer program (e.g., a general purpose computer configurable by a computer program or a microprocessor configurable by a computer program), electrical circuitry forming a memory device (e.g., any and all forms of random access memory), and electrical circuitry forming a communications device (e.g., a modem, communications switch, or optical-electrical equipment).

Figure 18:
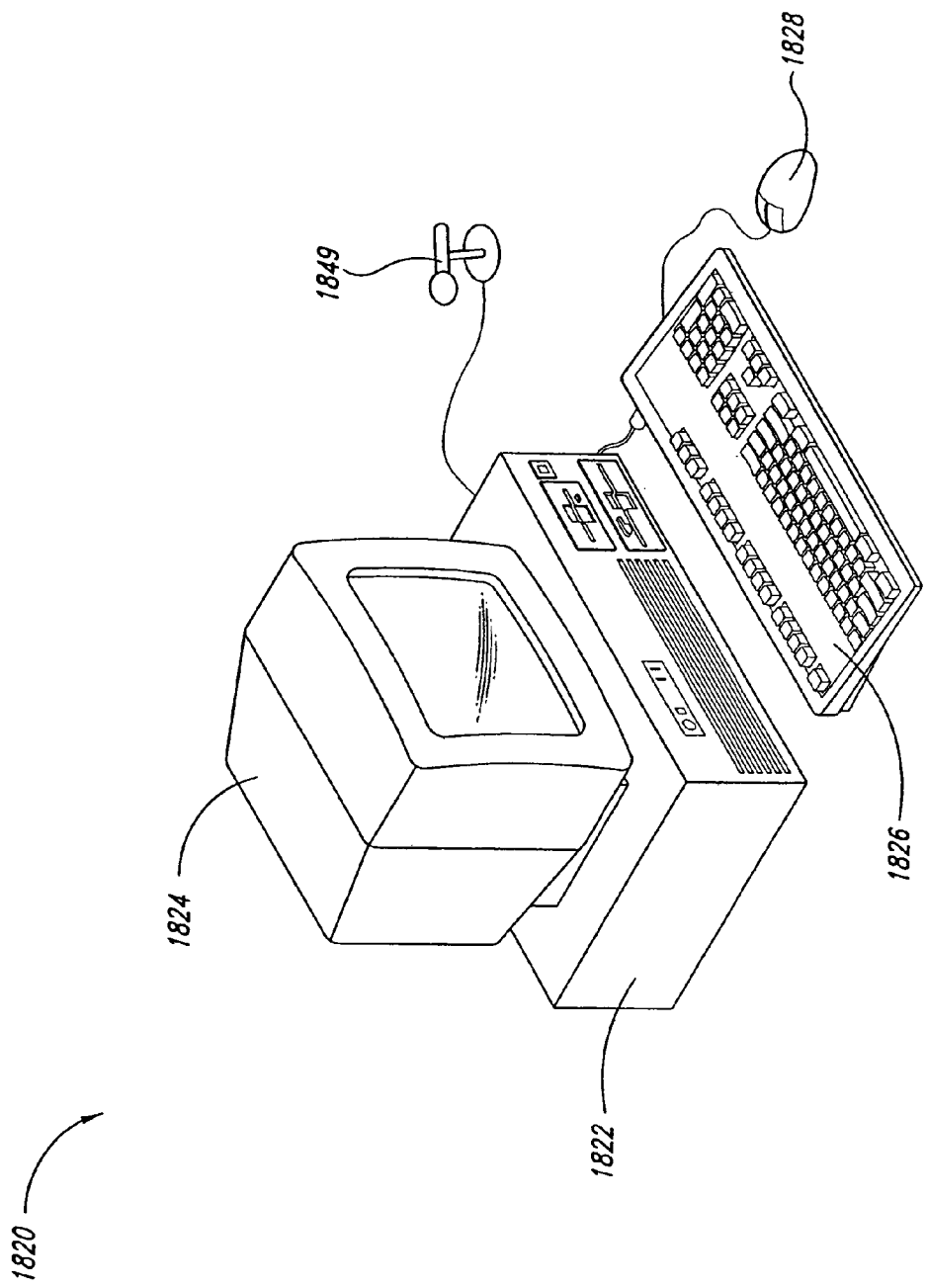
FIG. 18 depicts a pictorial representation of a conventional data processing system in which illustrative embodiments of the devices and/or processes described herein may be implemented.

Those skilled in the art will recognize that it is common within the art to describe devices and/or processes in the fashion set forth above, and thereafter use standard engineering practices to integrate such described devices and/or processes into data processing systems. That is, the devices and/or processes described above can be integrated into data processing system via a reasonable amount of experimentation. FIG. 18 shows an example representation of a data processing system into which the described devices and/or processes may be implemented with a reasonable amount of experimentation.

With reference now to FIG. 18, depicted a pictorial representation of a conventional data processing system in which illustrative embodiments of the devices and/or processes described herein may be implemented. It should be noted that a graphical user interface systems (e.g., Microsoft Windows 98 or Microsoft Windows NT operating systems) and methods can be utilized with the data processing system depicted in FIG. 18. Data processing system 1820 is depicted which includes system unit housing 1822, video display device 1824, keyboard 1826, mouse 1828, and microphone 1848. Further illustrated is that CCD-sensor 160 connects to a port (not shown) of data processing system 1820, such as a serial port or a USB (Universal Serial Bus) port. Data processing system 1820 may be implemented utilizing any suitable computer such as a DELL portable computer system, a product of Dell Computer Corporation, located in Round Rock, Tex.; Dell is a trademark of Dell Computer Corporation.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. For example, the height dimension of either or both holder portion 400 and stabilization portion 500 of CCD-array sensor positioning mechanism 100 can be varied (e.g., increased or decreased) should commercial venders begin making thinner or thicker CCD-array sensors than those discussed herein. Furthermore, it is to be understood that the invention is solely defined by the appended claims. It will be understood by those within the art that if a specific number of an introduced claim element is intended, such an intent will be explicitly recited in the claim, and in the absence of such recitation no such intent is present. For example, as an aid to understanding, the following appended claims may contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use of definite articles used to introduce claim elements. In addition, even if a specific number of an introduced claim element is explicitly recited, those skilled in the art will recognize that such recitation should typically be interpreted to mean at least the recited number (e.g., the bare recitation of "two elements," without other modifiers, typically means at least two elements, or two or more elements).

What is claimed is:

1. An apparatus comprising:
   a charge-coupled device (CCD)-array sensor having an active surface for recording images;
   a charge-coupled device(CCD)-array sensor positioning mechanism structured to hold said CCD-array in a substantially horizontal orientation such that the active surface for recording images is disposed substantially horizontally in a patient's mouth and structured to hold said CCD-array sensor in a first position to capture a first target area; and
   said CCD-array sensor positioning mechanism further structured to hold the substantially horizontally disposed CCD-array sensor in a second position to capture a second target area proximate to the first target area, the first and second target areas spatially related such that a first radiographic image recorded at the first target area may be combined with a second radiographic image recorded at the second target area to form a composite radiographic image substantially analogous to a single radiographic image of an aggregate target area covered by the first and second target areas.

2. The apparatus of claim 1, wherein the first and second target areas spatially related such that a first radiographic image recorded at the first target area may be combined with a second radiographic image recorded at the second target area to form a composite radiographic image substantially analogous to a single radiographic image of an aggregate target area covered by the first and second target areas further comprises:

the first and second target areas substantially co-extensive with at least a part of an occiusal view radiographic image.

3. The apparatus of claim 1, wherein the first and second target areas spatially related such that a first radiographic image recorded at the first target area may be combined with a second radiographic image recorded at the second target area to form a composite radiographic image substantially analogous to a single radiographic image of an aggregate target area covered by the first and second target areas further comprises:

the first target area proximate to the second target area.

4. The apparatus of claim 3, wherein the first target area proximate to the second target area further comprises:

the first target area substantially adjacent to the second target area.

5. The apparatus of claim 3, wherein the first target area proximate to the second target area further comprises:

the first target area overlapping the second target area.

6. The apparatus of claim 1, wherein said CCD-array sensor positioning mechanism further structured to position the CCD-array sensor to capture a second target area proximate to the first target area further comprises:

said CCD-array sensor positioning mechanism structured such that at least one CCD-array sensor is movable between a first position at which the CCD-array sensor will capture the first target area and a second position at which the CCD-array sensor will capture the second target area.

7. The apparatus of claim 6, wherein said CCD-array sensor positioning mechanism structured such that at least one CCD-array sensor is movable between a first position at which the CCD-array sensor will capture the first target area and a second position at which the CCD-array sensor will capture the second target area further includes:

the at least one CCD-array sensor slidable between the first and second positions.

8. The apparatus of claim 6, wherein said CCD-array sensor positioning mechanism structured such that at least one CCD-array sensor is movable between a first position at which the CCD-array sensor will capture the first target area and a second position at which the CCD-array sensor will capture the second target area further includes:

said CCD-array sensor positioning mechanism structured such that the at least one CCD-array sensor is movable between the first and second positions in substantially only one direction.

9. The apparatus of claim 6, wherein said CCD-array sensor positioning mechanism structured such that at least one CCD-array sensor is movable between a first position at which the CCD-array sensor will capture the first target area and a second position at which the CCD-array sensor will capture the second target area further includes:

at least one CCD-array sensor positioning block flipable between the first and second positions.

10. The apparatus of claim 1, wherein said CCD-array sensor positioning mechanism includes an impressionable portion to provide a repeatable position.

11. A method comprising:

positioning a charge-coupled device (CCD)-array sensor having an active surface for recording images in a patient's mouth such that said active surface is disposed substantially horizontally in said patient's mouth;

recording a first radiographic image of a first target area using a portion of said active surface of said charge coupled device (CCD)-array sensor, recording a second radiographic image of a second target area, the second target area proximate to the first target area, using the portion of the active surface of said CCD-array sensor; and displaying a composite image constructed from the first and second radiographic images.

12. The method of claim 11, wherein said recording a first radiographic image of a first target area using a portion of a CCD-array further comprises:

recording the first radiographic image of the first target area using the portion of the CCD-array positioned to cover the first target area.

13. The method of claim 11, wherein said recording a second radiographic image of a second target area, the second target area proximate to the first target area, using the portion of the CCD-array further comprises:

recording the second radiographic image of the second target area using the portion of the CCD-array positioned to cover the second target area.

14. The method of claim 11, wherein said displaying a composite image constructed from the first and second radiographic images further comprises:

producing a composite radiographic image substantially analogous to a single radiographic image of an aggregate target area covered by the first and second target areas.

15. The method of claim 14, wherein said producing a composite radiographic image substantially analogous to a single radiographic image of an aggregate target area covered by the first and second target areas further comprises:

producing a composite radiographic image substantially analogous to a single radiographic image of at least a part of an occlusal view radiographic image.

16. A method comprising:

situating a dental impression in at least a part of a charge-coupled device(CCD)-array sensor positioning mechanism on a dental surface;

situating a CCD-array sensor within the CCD-array sensor positioning mechanism to capture a first target area;

situating the CCD-array sensor within the CCD-array sensor positioning mechanism to capture a second target area proximate to the first target area, the first and second target areas spatially related such that a first radiographic image recorded at the first target area may be combined with a second radiographic image recorded at the second target area to form a composite radiographic image substantially analogous to a single radiographic image of an aggregate target area covered by the first and second target areas.

17. The method of claim 16, further comprising:

forming the dental impression in a stabilization portion of the at least a part of a CCD-array sensor positioning mechanism.

18. A system comprising:

means for holding a charge-coupled device (CCD)-array sensor having an active surface for recording images inside a patient's mouth such that said active surface is disposed substantially horizontally in said patient's mouth;

means for recording a first radiographic image of a first target area using a portion of said active surface of said charge coupled device (CCD)-array sensor;

means for recording a second radiographic image of a second target area, the second target area proximate to the first target area, using the portion of the active surface of said CCD-array; and means for displaying a composite image constructed from the first and second radiographic images.

19. The system of claim 18, wherein said means for recording a first radiographic image of a first target area using a portion of a CCD-array further comprises:

means for recording the first radiographic image of the first target area using the portion of the CCD-array positioned to cover the first target area.

20. The system of claim 18, wherein said means for recording a second radiographic image of a second target area, the second target area proximate to the first target area, using the portion of the CCD-array further comprises:

means for recording the second radiographic image of the second target area using the portion of the CCD-array positioned to cover the second target area.

21. The system of claim 18, wherein said means for displaying a composite image constructed from the first and second radiographic images further comprises:

means for producing a composite radiographic image substantially analogous to a single radiographic image of an aggregate target area covered by the first and second target areas.

22. The system of claim 21, wherein said means for producing a composite radiographic image substantially analogous to a single radiographic image of an aggregate target area covered by the first and second target areas further comprises:

means for producing a composite radiographic image substantially analogous to a single radiographic image of at least a part of an occiusal view radiographic image.

23. An apparatus for imaging a patient's teeth comprising:
a horizontally and vertically movable radiation source;
an intra-oral sensor having an active surface of pixels capable of recording an image disposed horizontally in a patient's mouth; said sensor generating output signals representing sensor information corresponding to the amount of radiation arriving at each of the pixels;
a storage medium for storing the sensor information; and
image processing circuitry for processing an image from said sensor information stored on said storage medium.

24. The apparatus of claim 23, wherein said radiation source is positioned in a first position such that a first set of output signals is collected and positioned in a second position such that a second set of output signals is collected, whereby said image processing circuitry combines sensor information for each set of output signals into a composite image.

25. The apparatus of claim 23, wherein said sensor is positioned in a first position such that a first set of output signals is collected and positioned in a second position such that a second set of output signals is collected, whereby said image processing circuitry combines sensor information for each set of output signals into a composite image.

26. The apparatus of claim 23, wherein said image is an occlusal view.

27. An apparatus for imaging a patient's teeth comprising:
a radiation source;
an intra-oral sensor having an active surface of pixels; said sensor generating output signals representing sensor information corresponding to the amount of radiation arriving at each of the pixels;
an impressionable portion associated with said sensor to provide repeatable positioning of said portion;
a storage medium for storing the sensor information; and
image processing circuitry for processing an image from said sensor information stored on said storage medium.

28. An apparatus for imaging a patient's teeth comprising:
an irradiating means for irradiating a first target area and a second target area;
an intra-oral sensing means having an active surface of pixels;
positioning means for orienting said active surface of pixels substantially horizontal in a patient's mouth in a first position to capture an image of said first target area and a second position to capture an image of said second target area;
recording means for recording said images; and
imaging means for processing a composite image of said images.

* * * * *

UNITED STATES PATENT AND TRADEMARK OFFICE
CERTIFICATE OF CORRECTION

PATENT NO. : 7,010,089 B2 Page 1 of 1
DATED : March 7, 2006
INVENTOR(S) : Steven L. Eikenberg It is certified that error appears in the above-identified patent and that said Letters Patent is hereby corrected as shown below:

<u>Column 1,</u>
Line 11, change "2002" to -- 2000 --.

Signed and Sealed this

Thirtieth Day of May, 2006

JON W. DUDAS
*Director of the United States Patent and Trademark Office*